(12) United States Patent
Howarth

(10) Patent No.: US 8,759,488 B2
(45) Date of Patent: Jun. 24, 2014

(54) HIGH STABILITY STREPTAVIDIN MUTANT PROTEINS

(75) Inventor: Mark Howarth, Oxford (GB)

(73) Assignee: Isis Innovation Limited, Summertown (GB)

( * ) Notice: Subject to any disclaimer, the term of this patent is extended or adjusted under 35 U.S.C. 154(b) by 0 days.

(21) Appl. No.: 13/504,540

(22) PCT Filed: Oct. 28, 2010

(86) PCT No.: PCT/GB2010/002006
§ 371 (c)(1),
(2), (4) Date: Apr. 27, 2012

(87) PCT Pub. No.: WO2011/051680
PCT Pub. Date: May 5, 2011

(65) Prior Publication Data
US 2012/0214970 A1    Aug. 23, 2012

(30) Foreign Application Priority Data
Oct. 30, 2009 (GB) .................................. 0919102.4

(51) Int. Cl.
*C07K 17/00* (2006.01)

(52) U.S. Cl.
USPC .......................................................... 530/367

(58) Field of Classification Search
None
See application file for complete search history.

(56) References Cited

U.S. PATENT DOCUMENTS 6,103,493 A * 8/2000 Skerra et al. ................. 435/69.1
7,265,205 B2 * 9/2007 Wu et al. ........................ 530/350

OTHER PUBLICATIONS

Murakami et al., "Site-Directed Incorporation of Fluorescent Nonnatural Amino Acids into Streptavidin for Highly Sensitive Detection of Biotin", Biomacromolecules 2000, 1, 118-125.*

Watanabe et al., "Four-Base Codon-Mediated Saturation Mutagenesis in a Cell-Free Translation System", Journal of Bioscience and Bioengineering, 2008, vol. 105, No. 3, 211-215.*

Airaksinen et al., "Modified Base Compositions at Degenerate Positions of a Mutagenic Oligonucleotide Enhance Randomness in Site-Saturation Mutagenesis", Nuc. Acid. Res., 1998, vol. 26(2):576-581.*

Myer et al, "Reduced antibody response to streptavidin through site-directed mutagenesis", Protein Science, 10 (3):491-503 (2001).

Levy et al, Directed evolution of streptavidin variants using in vitro compartmentalization, Chemistry & Biology, 15 (9):979-989 (2008).

Korndoerfer et al, "Improved affinity of engineered streptavidin for the Strep-tag II peptide is due to a fixed open conformation of the lid-like loop at the binding site", Protein Science, 11(4):883-893 (2002).

Chivers et al, "A streptavidin variant with slower biotin dissociation and increased mechanostability", Nature Methods, 7(5):391-393+3pp (May 2010).

Chivers et al, "Stickier than streptavidin", Assay and Drug Development Technologies, 8(3):278-279 (Jun. 1, 2010).

* cited by examiner

*Primary Examiner* — Suzanne M Noakes
(74) *Attorney, Agent, or Firm* — Porter Wright Morris & Arthur LLP

(57) ABSTRACT

The present invention provides a mutant streptavidin subunit which comprises one or more amino acid substitutions compared to a wildtype streptavidin subunit at any one of residue positions equivalent to positions (50, 51, 52, 53) and (54) of SEQ ID NO. 2 and wherein amino acid residues at positions equivalent to positions (23, 27, 43, 45, 49, 79, 88, 90, 92, 108, 110) and (128) of SEQ ID NO. 2, in said mutant streptavidin subunit, are wildtype, wherein (i) when said mutant streptavidin subunit unit is comprised in streptavidin, said streptavidin has a lower off rate for biotin or for a biotin conjugate than wildtype streptavidin or (ii) when said mutant streptavidin subunit is in monomelic form said mutant monomelic streptavidin has a lower off rate for biotin or a biotin conjugate than monomelic streptavidin. The invention also encompasses nucleic acid molecules comprising a nucleotide sequence encoding the mutant streptavidin subunit and vectors and cells comprising the nucleic acid. Further, methods of capturing biotinylated molecules and cells and therapeutic methods are encompassed.

13 Claims, 12 Drawing Sheets

Streptavidin + biotin

Streptavidin − biotin

Figure 9 (SEQ ID NO: 1)

MRKIVVAAIAVSLTTVSITASASADPSKDSKAQVSAAEAGITGTWYNQLGST
FIVTAGADGALTGTYESAVGNAESRYVLTGRYDSAPATDGSGTALGWTVA
WKNNYRNAHSATTWSGQYVGGAEARINTQWLLTSGTTEANAWKSTLVGH
DTFTKVKPSAASIDAAKKAGVNNGNPLDAVQQ

Figure 10 (SEQ ID NO: 2)

DPSKDSKAQVSAAEAGITGTWYNQLGSTFIVTAGADGALTGTYESAVGNAE
SRYVLTGRYDSAPATDGSGTALGWTVAWKNNYRNAHSATTWSGQYVGG
AEARINTQWLLTSGTTEANAWKSTLVGHDTFTKVKPSAASIDAAKKAGVN
NGNPLDAVQQ

Figure 11A (SEQ ID NO: 3)

AEAGITGTWYNQLGSTFIVTAGADGALTGTYESAVGNAESRYVLTGRYDSA
PATDGSGTALGWTVAWKNNYRNAHSATTWSGQYVGGAEARINTQWLLTS
GTTEANAWKSTLVGHDTFTKVKPSAAS

Figure 11B (SEQ ID NO: 4)

AEAGITGTWYNQLGSTFIVTAGADGALTGTYESAVGNAESRYVLTGRYDSA
PATDGSGTALGWTVAWKNNYRNAHSATTWSGQYVGGAEARINTQWLLTS
GTTEANAWKSTLVGHDTFTKVKPSAASHHHHHH

Figure 12

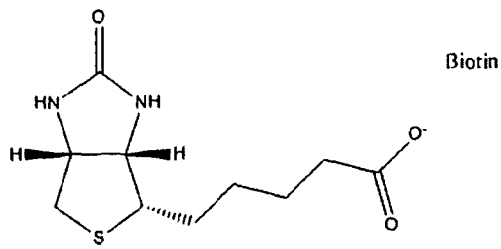
Biotin

Figure 13A (SEQ ID NO: 5)

AEAGITGTWYNQLGSTFIVTAGADGALTGTYESAVGNAEGDYVLTGRYDS
APATDGSGTALGWTVAWKNNYRNAHSATTWSGQYVGGAEARINTQWLLT
SGTTEANAWKSTLVGHDTFTKVKPSAAS

Figure 13B (SEQ ID NO: 8)

AEAGITGTWYNQLGSTFIVTAGADGALTGTYESAVGNAEGDYVLTGRYDS
APATDGSGTALGWTVAWKNNYRNAHSATTWSGQYVGGAEARINTQWLLT
SGTTEANAWKSTLVGHDTFTKVKPSAASHHHHHH

Figure 14 (SEQ ID NO: 6)

AEAGITGTWYNQLGSTFIVTAGADGALTGTYESAVGNAEGSYVLTGRYDSA
PATDGSGTALGWTVAWKNNYRNAHSATTWSGQYVGGAEARINTQWLLTS
GTTEANAWKSTLVGHDTFTKVKPSAAS

Figure 15 (SEQ ID NO: 7)

AEAGITGTWYNQLGSTFIVTAGADGALTGTYESAVGNAEGNYVLTGRYDS
APATDGSGTALGWTVAWKNNYRNAHSATTWSGQYVGGAEARINTQWLLT
SGTTEANAWKSTLVGHDTFTKVKPSAAS

HIGH STABILITY STREPTAVIDIN MUTANT PROTEINS

RELATED APPLICATION

The present application is a 371 of PCT/GB2010/002006 filed Oct. 28, 2010.

Streptavidin, a protein produced by *Streptomyces avidinii*, binds to the water soluble vitamin biotin with a very high affinity. Streptavidin is a tetrameric protein where the interaction between biotin and streptavidin is one of the most commonly used in biological research. Biotin binding proteins have been isolated from a wide range of species but streptavidin shows the most stable binding to biotin conjugates of all of these (Laitinen et al, 2006, Cell Mol. Life Sci., 63, 2992-3017; Nordlund et al, 2005, J. Biol. Chem., 280, 13250-13255). Streptavidin is used in imaging, purification, immobilisation, immunoassays and nano-assembly, while also showing success in cancer clinical trials for drug targeting (Sakahara and Saga, 1999, Adv. Drug Deliv. Rev., 37, 89-101; Goldenberg et al, 2006, J. Clin. Oncol., 24, 823-834; Wilbur et al, 1999, Biomol. Eng., 16, 113-118). High affinity is not the only important feature of the streptavidin-biotin interaction. The fast on-rate (association rate) allows rapid capture of biotinylated targets even at low concentrations and at 4° C. In addition, streptavidin and biotin show low non-specific binding and biotinylation generally does not disrupt biomolecule function. The streptavidin-biotin interaction is resilient up to 90° C., from pH 3-11, at diverse ionic strengths, in 6M guanidinium hydrochloride and in sodium dodecyl sulfate. Another advantage of streptavidin over other stable targeting methods, such as HaloTag or the SNAP-tag is that its ligand can be precisely targeted to proteins using *E. coli* biotin ligase in vitro, in cells and in living animals. These properties have also led to the further advantage that a large variety of streptavidin and biotin conjugates and reagents for biotinylation are commercially available.

Nevertheless, the perception that the streptavidin-biotin interaction is essentially irreversible under typical experimental conditions (4-37° C., pH 5-8) is far from correct. In cellular imaging applications, dissociation of streptavidin may be detected after two hours, accelerated by the low pH of endosomes (Bruneau et al, 2005, J. Neurosci., 25, 9949-9959). In nanotechnology applications, nanoparticle attachment causes a surprising decrease in streptavidin-biotin stability (Swift et al, 2006, Biophys. J., 90, 1396-1410; Swift and Cramb, 2008, Biophys. J., 95, 865-876), with the half-time for dissociation from biotinylated polystyrene beads reduced to 20 seconds (Buranda et al, 1999, Cytometry, 37, 21-31). For investigating molecular motors, streptavidin was displaced by the translocation of helicases (Morris et al, 2001, Methods, 23, 149-159), transcription terminator rho (Schwartz et al, 2007, J. Biol. Chem., 282, 31469-31476), or RNA polymerase (Fujita and Silver, 1993, Biotechniques, 14, 608-617). Streptavidin is also used at high temperatures with thermal cycling for DNA amplification and biotinylated DNA had to be bis-biotinylated to reduce dissociation (Dressman et al, 2003, Proc. Natl. Acad. Sci. USA, 100, 8817-8822). The streptavidin-biotin interaction is therefore not irreversible and dissociation of streptavidin from biotin conjugates occurs in many contexts.

In many situations such a dissociation is undesired. For example in cell imaging methods, it would be advantageous to be able to detect streptavidin-biotin binding a long time after the initial binding has occurred and thus for dissociation to be minimal. In this way, it would be potentially possible to image cells many hours or days after the initial staining of the cells. Further, minimal dissociation of streptavidin from biotin would be advantageous when targeting drugs for cancer therapy. Hence, a streptavidin mutant with a tighter interaction to biotin conjugates and thus a slower dissociation therefrom would be advantageous for many uses.

In a highly optimised system, almost any change will reduce performance. This has been shown in the streptavidin-biotin system, where more than 200 mutants of streptavidin have been made in the art but none of the mutants have improved affinity for free biotin (Laitinen et al, supra). Computational modelling suggested that streptavidin might bind better to 9R-methylbiotin than to biotin, but this was not borne out by experiment (Dixon et al, 2002, J. Org. Chem., 67, 1827-1837). Streptavidin libraries have been screened by phage display and in vitro compartmentalisation, which yielded a streptavidin variant with improved affinity for desthiobiotin but no pair with an interaction as strong as the wildtype streptavidin-biotin interaction (Levy and Ellington, 2008, Chem. Biol., 15, 979-989). A streptavidin mutant was engineered to contain a cysteine that could form a disulfide bond with a thiol-linked biotin conjugate, giving controlled reversibility (Wu et al, 2009, J. Biol. Chem., 280, 23225-23231), although this streptavidin mutant will only give enhanced binding to certain biotin conjugates and to systems unaffected by changing redox, which excludes use on cells.

Monomeric streptavidin which cannot tetramerise has been reported in the art, where streptavidin subunits can for example be produced by making the mutations T76R, V125R, V55T and L109T. The advantage of using monomeric streptavidin lies in its small size which is beneficial for imaging and that it can be genetically targeted for fusion to a specific protein without inducing multimerisation of that protein. However, monomeric streptavidin has the disadvantage that it has a higher off rate from biotin than wildtype tetrameric streptavidin. Thus monomeric streptavidin will dissociate much more readily from biotin which may be particularly undesirable in applications such as cell imaging.

The present inventors have now engineered streptavidin mutant subunits which surprisingly have a lower off rate from biotin conjugates, when in tetrameric form, than wildtype streptavidin. Advantageously, the streptavidin mutant subunits when in tetrameric form therefore dissociate more slowly from biotin than their counterparts and are hence extremely useful in applications where sustained binding is required. As discussed previously, no streptavidin mutants have previously been identified as having a lower off rate for biotin despite over 200 different mutants having been developed.

In one aspect, the present invention therefore provides a mutant streptavidin subunit which comprises one or more amino acid substitutions compared to a wildtype streptavidin subunit at any one or more of residue positions equivalent to positions 50, 51, 52, 53 and 54 of SEQ ID NO. 2 and wherein amino acid residues at positions equivalent to positions 23, 27, 43, 45, 49, 79, 88, 90, 92, 108, 110 and 128 of SEQ ID NO. 2, in said mutant streptavidin subunit, are wildtype, wherein (i) when said mutant streptavidin subunit is comprised within streptavidin, said streptavidin has a lower off rate for biotin or for a biotin conjugate than wildtype streptavidin or (ii) when said mutant streptavidin subunit is in monomeric form, said mutant monomeric streptavidin has a lower off rate for biotin or for a biotin conjugate than monomeric streptavidin.

In a further aspect, a mutant streptavidin comprising at least one mutant streptavidin subunit as described above is provided.

Thus, the term "streptavidin" or "streptavidin protein" as used herein refers to streptavidin comprising four streptavidin subunits. Particularly, streptavidin may be a tetrameric protein comprising four streptavidin subunits where the individual subunits multimerise (e.g. tetramerise) together to form streptavidin. Alternatively, streptavidin may be a single chain polypeptide comprising four streptavidin subunits in a single chain. For the tetrameric protein, a nucleic acid sequence may encode an individual subunit(s) which is then translated into a single subunit polypeptide. The individual subunits then multimerise as discussed above to form the tetrameric protein. For the single chain streptavidin polypeptide, a single nucleic acid sequence encoding four streptavidin subunits is expressed, where the four streptavidin subunits may be separated from each other by one or more linkers. This results in the production of a single polypeptide chain comprising the four subunits.

The "mutant streptavidin" of the invention as described above, comprises at least one mutant streptavidin subunit of the invention. The mutant streptavidin may therefore comprise 2, 3 or 4 mutant streptavidin subunits of the invention. Where the mutant streptavidin comprises 1, 2 or 3 mutant subunits of the invention, the other 3, 2, or 1 subunits, respectively present may be wildtype or comprise mutations which do not result in the final streptavidin having an increased off rate for biotin than wildtype streptavidin. Alternatively, the other 3, 2 or 1 subunits may be inactivated for biotin binding. Inactivating the other subunits in such a way will not affect the stability of biotin binding to the mutant streptavidin subunit in the mutant streptavidin, as long as there is no change in the subunit interface.

Thus, the mutant streptavidin may be monovalent i.e. only has one biotin binding site (where the valency of streptavidin refers to the number of biotin binding subunits present in the protein). Monovalent mutant streptavidin may therefore comprise one mutant streptavidin subunit of the invention together with 3 inactivated streptavidin subunits. Divalent, trivalent, and tetravalent mutant streptavidins can also be used, which have 2, 3, and 4 biotin binding subunits, respectively, one or more of which will be the mutant streptavidin subunit of the invention.

Preferably, the mutant streptavidin of the invention comprises four mutant streptavidin subunits of the invention or comprises 1 or 2 mutant streptavidin subunits of the invention, together with 3 or 2 inactivated streptavidin subunits which cannot bind biotin, respectively.

As discussed above, the mutant streptavidin may be a tetrameric protein formed by the multimerisation of four streptavidin subunits, at least one of which is a mutant streptavidin subunit of the invention, or may be a single chain polypeptide comprising four streptavidin subunits in one chain, at least one of which is a mutant streptavidin subunit of the invention.

"Wildtype streptavidin" refers to the wildtype streptavidin protein comprising four wildtype streptavidin subunits as defined further below. Wildtype streptavidin may be in the form of the tetrameric protein formed by the multimerisation of 4 wildtype streptavidin subunits or may be a single chain polypeptide comprising 4 wildtype streptavidin subunits i.e. a single chain tetravalent streptavidin.

Reference to a "streptavidin subunit" as used herein refers to a single streptavidin subunit which is not multimerised and is not present in tetrameric form.

Thus, the mutant streptavidin of the invention has a lower off rate or dissociates more slowly from biotin than wildtype streptavidin. It is further proposed that when the mutant streptavidin subunit of the invention is in monomeric form, it has a lower off rate than monomeric streptavidin. The lower off rate is achieved by the substitution of one or more of the naturally occurring amino acids at positions 50 to 54 in a streptavidin subunit with a different amino acid, whilst maintaining a wildtype biotin binding pocket i.e. retaining wildtype amino acid residues at positions 23, 27, 43, 45, 49, 79, 88, 90, 92, 108, 110 and 128 in the streptavidin subunit.

Thus, the mutant streptavidin subunits of the invention are modified compared to wildtype streptavidin subunits to achieve the lower off rate for biotin and are hence obtained or prepared by modifying streptavidin subunits and preferably by introducing one or more of the amino acid substitutions described above.

Hence, the term "wildtype streptavidin subunit" as used herein includes all forms of wildtype streptavidin subunits including full length and truncated sequences as discussed below. The sequence of the wildtype full length streptavidin subunit is well known in the art and consists of an amino acid sequence as set forth in SEQ ID NO. 1. This full length sequence is usually truncated at the N and C-terminal ends to remove signal peptides and the production of streptavidin by *Streptomyces avidinii* may result in the production of a mixture of protein chains from the endogenous cleavage of full length streptavidin subunits.

In particular, the full length sequence may be truncated to produce the mature streptavidin subunit sequence which is 159 amino acids in length and begins at amino acid position 25 in the full length sequence (SEQ ID NO. 1). The universal numbering of residues within the streptavidin subunit begins at the first residue of the mature streptavidin subunit sequence. Thus, alternatively viewed, residue 25 in the full length subunit sequence is defined as residue 1. The mature streptavidin subunit sequence is set forth in SEQ ID NO. 2.

This mature sequence may be further truncated and particularly may be truncated to produce the core streptavidin subunit sequence (also known as natural core streptavidin). The core streptavidin subunit sequence begins at residue 13 of the mature streptavidin subunit sequence and is a fragment of the mature sequence consisting of residues 13 to 139 of SEQ ID NO. 2. The sequence of core streptavidin subunit is set forth in SEQ ID NO. 3. Further truncations can be made from the core sequence, e.g. fragments consisting of residues 14 to 138 and 16 to 133 of the mature streptavidin subunit sequence have been produced and shown to function (Sano et al, 1995, J. Biol. Chem., 270, 28204-28209).

Although streptavidin usually occurs in tetrameric form, as discussed above, monomeric streptavidin can be generated which is unable to multimerise i.e. tetramerise. Thus, reference to streptavidin in monomeric form or to monomeric streptavidin refers to a streptavidin subunit which is unable to tetramerise and which only occurs as individual subunits. Monomeric streptavidin may be unable to tetramerise if isolated as a single molecule, if used a high temperatures or may be produced by mutating the wildtype streptavidin subunit sequence at one or more residues. Typically, monomeric streptavidin is produced by making one or more amino acid substitutions at residue positions equivalent to positions 76, 125, 55 or 109 in SEQ ID NO. 2. Preferably, monomeric streptavidin may comprise the mutations; T76R, V125R, V55T and L109T (see U.S. Pat. No. 7,265,205). Thus, the mutant streptavidin subunit of the invention when in monomeric form will be unable to form tetramers and may additionally comprise one or more amino acid substitutions at residues 76, 125, 55 and 109. The mutant streptavidin subunit of the invention when in monomeric form will preferably comprise T76R, V125R, V55T and L109T amino acid substitutions in addition to the amino acid substitutions discussed above i.e. in addition to the one or more mutations at positions 50 to 54.

In a further embodiment, the invention also provides a mutant streptavidin subunit of the invention in monomeric form.

The mutant streptavidin subunit of the present invention thus comprises one or more mutations compared to a wildtype streptavidin subunit i.e. compared to SEQ ID NOs 1, 2 or 3, at residue positions in the mutant streptavidin subunit which are equivalent to positions 50-54 in SEQ ID NO. 2. Although other modifications may be made to the mutant streptavidin subunit compared to the wildtype sequences in addition to the mutations to any one or more of the residues at 50 to 54, the mutant must either have a lower off rate for biotin than wildtype streptavidin when the subunit is comprised within streptavidin e.g. is in tetrameric form or have a lower off rate for biotin than monomeric streptavidin when said mutant subunit is in monomeric form. Thus, the mutant subunit may have other mutations, i.e. insertions, deletions, substitutions etc as compared to the wildtype subunit sequence in addition to the mutations at positions 50 to 54. Further, the mutant streptavidin subunit may have N and/or C terminal extensions and may thus have a longer sequence than a wildtype streptavidin subunit. For example, the mutant streptavidin subunit may contain a His tag. Particularly, however, if any other mutations are present, these may be conservative amino acid substitutions.

As discussed above, the mutant streptavidin subunit must have wildtype residues present at positions 23, 27, 43, 45, 49, 79, 88, 90, 92, 108, 110 and 128 i.e. identical residues found at these positions in SEQ ID NO. 2 must be present at equivalent positions in the mutant streptavidin subunit (or conservative amino acid substitutions of such residues which do not affect the formation of the biotin binding site). The residues at positions 23, 27, 43, 45, 49, 79, 88, 90, 92, 108, 110 and 128 in SEQ ID NO. 2 are as follows:

Asn 23, Ser 27, Tyr 43, Ser 45, Asn 49, Trp 79, Ser 88, Thr 90, Trp 92, Trp 108, and Asp 128 and thus these amino acids should preferably be found at equivalent positions in the mutant streptavidin subunit.

These amino acid residues are important for the formation of the biotin binding site in the mutant streptavidin subunit. Additionally, when the subunit is comprised within streptavidin e.g. in tetrameric form, a further residue which is provided by an adjacent subunit in streptavidin may help form the biotin binding site, namely Trp 120. Thus, in streptavidin each subunit provides a Trp 120 residue for an adjacent subunit (as shown in FIG. 3). For a tetravalent streptavidin protein, all subunits may comprise a wildtype Trp 120 residue or have only a conservative amino acid substitution at this position.

Preferably therefore, when the mutant streptavidin subunit of the invention is comprised within streptavidin e.g. is in tetrameric form, a wildtype residue is present at a position equivalent to position 120 in SEQ ID NO. 2, in another adjacent subunit in the streptavidin to allow stable biotin binding with the mutant streptavidin subunit. Thus, as discussed above, an adjacent streptavidin subunit preferably contributes a Trp 120 residue to the biotin binding site of the mutant streptavidin subunit in the tetramer. The particular adjacent subunit which provides the Trp 120 residue to the mutant streptavidin subunit depends on the positioning of the mutant subunit in streptavidin. As shown in FIG. 3, for biotin bound to subunit 1 of the tetramer, the "adjacent" subunit to provide the 120 residue is subunit 2. Thus, if the mutant streptavidin subunit is situated at subunit 1 in FIG. 3, then preferably, the amino acid residue at a position equivalent to position 120 of SEQ ID NO. 2 in subunit 2 is wildtype i.e. is Trp, or a conservative substitution is present at this position. The amino acid residues at positions equivalent to positions 120 of SEQ ID NO. 2 in the other subunits i.e. in subunits 1, 3 and 4 do not need to be wildtype and may be mutated. Therefore, when the mutant streptavidin subunit is comprised in streptavidin, preferably at least the adjacent subunit (as shown in FIG. 3) has a wildtype residue or a conservative amino acid substitution at a position equivalent to position 120 of SEQ ID NO. 2. Further, the other subunits may also have a wildtype residue or a conservative amino acid substitution at a position equivalent to position 120 of SEQ ID NO. 2, particularly, where the streptavidin is divalent, trivalent or tetravalent i.e. has 2, 3, or 4 biotin binding sites. Thus, for tetravalent streptavidin, all subunits, including the mutant streptavidin subunits of the invention may have a wildtype residue or a conservative amino acid substitution at a position equivalent to position 120 of SEQ ID NO. 2

Thus, the mutant streptavidin subunit of the present invention particularly may be at least 70% identical to the wildtype streptavidin subunit sequences as set forth in SEQ ID NOs 1, 2 or 3 and more particularly is at least 75, 80, 85, 90, 95, 96, 97, 98 or 99% identical to SEQ ID NOs 1, 2 or 3. The mutant streptavidin subunit thus encompasses mutant forms of streptavidin homologue subunits which are structurally similar to streptavidin subunits and are able to interact with biotin when tetramerised. In cases where a mutant streptavidin homologue subunit is produced or where the mutant streptavidin subunit comprises other mutations, e.g. deletions or insertions, in addition to the one or more substitutions at positions 50-54, the substitutions at one or more of amino acid residue positions 50 to 54 are carried out at equivalent amino acid residues in the homologue or mutant subunit sequences. Further, the wildtype residues at positions 23, 27, 43, 45, 49, 79, 88, 90, 92, 108, 110 and 128 occur at equivalent amino acid positions in the homologue or mutant subunit sequences. An equivalent position is determined by reference to the amino acid sequence of SEQ ID NO. 2 i.e. the mature streptavidin subunit sequence which dictates the numbering of the amino acid residues in streptavidin. The homologous or corresponding position can be readily deduced by lining up the sequence of the homologue or mutant subunits and the sequence of SEQ ID NO. 2 based on the homology or identity between the sequences for example using a BLAST algorithm. Therefore, the parental and new sequence can be entered at the following weblink to line up the sequences and determine corresponding positions: http://blast.ncbi.nlm.nih.gov/Blast.cgi?PAGE_TYPE=BlastSearch&PROG_DEF=blastn&BLAST_PROG_DEF=megaBlast&BLAST_SPEC=blast2seq.

Amino acid sequence identity (or similarity) may also be determined using the BESTFIT program of the Genetics Computer Group (GCG) Version 10 Software package from the University of Wisconsin. The program uses the local homology algorithm of Smith and Waterman with the default values: Gap creation penalty=, Gap extension penalty=2, Average match=2.912, Average mismatch=2.003. The PILEUP and BLAST algorithms can be used to calculate homology or line up sequences. Software for performing BLAST analyses is publicly available through the National Center for Biotechnology Information (http://www.ncbi.nlm.nih.gov/). Particularly, in the present invention, identity is compared over the whole amino acid sequence.

Thus, the amino acid position numbering referred to with respect to the mutant streptavidin subunit may not be the actual numbering of amino acids within that subunit. The numbering used relates to the position of amino acids in the mature streptavidin sequence of SEQ ID NO. 2 and as discussed above, equivalent residue positions are intended in the mutant subunits of the invention. Therefore, although the one or more amino acid substitutions may occur at residue positions 50-54 in the mutant streptavidin subunit e.g. if its sequence is the same length as that of SEQ ID NO. 2, if the sequence is a different length to SEQ ID NO. 2, the amino acid substitution(s) will take place at the equivalent residue(s). For example, if the mutant streptavidin subunit is based on the core streptavidin sequence which has a 12 amino acid truncation at the N terminus compared to the mature sequence of SEQ ID NO. 2, then the one or more amino acid substitutions will occur at positions 38-42 in that sequence which correspond to positions 50-54 of SEQ ID NO. 2. Thus reference herein to amino acid residue positions 50-54 of mutant streptavidin subunit refers to amino acid residue positions in the mutant streptavidin subunit which are equivalent to those at positions 50-54 in SEQ ID NO. 2.

Similarly, although the wildtype residues may occur at positions 23, 27, 43, 45, 49, 79, 88, 90, 92, 108, 110 and 128 in the mutant streptavidin subunit if this has a sequence the same length as SEQ ID NO. 2, if the sequence of the mutant subunit is a different length, then the equivalent residues at those positions in the mutant subunit will be wildtype.

Hence, any modification or combination of modifications may be made to a wildtype streptavidin subunit to produce the mutant streptavidin subunit of the invention, provided that the mutant comprises an amino acid substitution at any one or more of amino acid residues positions equivalent to positions 50 to 54 of SEQ ID NO. 2, has wildtype amino acid residues at positions equivalent to positions 23, 27, 43, 45, 49, 79, 88, 90, 92, 108, 110 and 128 of SEQ ID NO. 2 and has a lower off rate for biotin than wildtype streptavidin when the mutant streptavidin subunit is comprised within streptavidin or has a lower off rate for biotin than monomeric streptavidin when in monomeric form.

Thus a mutant streptavidin subunit of the present invention may differ from the wild type streptavidin subunit sequences by for example 1 to 20, 1 to 10, 1 to 8, 1 to 6, 1 to 5, 1 to 4, 1 to 3 or 1 to 2 amino acid substitutions, insertions and/or deletions. When a mutation is made to the mutant streptavidin subunit outside of the 50-54 amino acid region (or equivalent region), it is preferred as described above that the mutation is a conservative amino acid substitution. Thus, although the substituted amino acid may be any one of the well known 20 conventional amino acids (Ala (A), Cys (C), Asp (D), Glu (E), Phe (F), Gly (G), H is (H), Ile (I), Lys (K), Leu (L), Met (M), Asn (N), Pro (P), Gln (O), Arg (R), Ser (S), Thr (T), Val (V), Trp (W) and Tyr (Y)), when the mutation is made outside the 50-54 region (or equivalent region), it is preferred that an amino acid is replaced by another which preserves the physiochemical character of the polypeptide (e.g. D may be replaced by E or vice versa, N by Q, or L; I by V or vice versa). Thus, generally the substituting amino acid has similar properties e.g. hydrophobicity, hydrophilicity, electronegativity, bulky side chains etc to the amino acid being replaced when such substitution is outside of the 50-54 region. Isomers of the native L-amino acid e.g. D-amino acids may be incorporated.

Alternatively, other modifications which can be made to the wildtype streptavidin subunit outside of the 50-54 amino acid region (or equivalent region) include further truncations of the subunit. For example, truncated streptavidin subunits consisting of residues 16-133 and 14-138 of the mature sequence of SEQ ID NO. 2 can be used or other truncations which result in the production of a mutant subunit having the properties required by the present invention.

As discussed above, the mutant streptavidin subunit of the invention comprises one or more amino acid substitutions at amino acid residue positions equivalent to positions 50, 51, 52, 53 or 54 of SEQ ID NO. 2. Thus, any one or more of the wildtype amino acid residues found at positions 50, 51, 52, 53 or 54 (or the equivalent positions) may be substituted with any other natural or non-natural amino acid residue.

The amino acid residues which are substituted into any one or more of positions 50 to 54 may be any amino acid residues. Thus, for example, any of the 20 conventional amino acid residues set out above can be substituted into any one or more of positions 50, 51, 52, 53 and/or 54. Particularly, an amino acid residue with a different side chain polarity and/or a different side chain acidity or basicity to the amino acid residue found in the wildtype streptavidin subunit sequence may be substituted into the mutant streptavidin subunit.

Thus, for example, the following amino acid residues are found in wildtype streptavidin subunit at positions 50-54; alanine (non-polar neutral amino acid) at position 50, glutamic acid (polar acidic amino acid) at position 51, serine (polar neutral amino acid) at position 52, arginine (polar basic amino acid) at position 53 and tyrosine (non-polar neutral amino acid) at position 54. It is preferred therefore, that the amino acid residues which substitute any one or more of these wildtype residues have a different polarity or acidity.

For example at position 50, the substituting amino acid may be polar and/or basic and/or acidic e.g. may be asparagine, aspartic acid etc, and is preferably not a non-polar neutral amino acid such as glycine, isoleucine, leucine, methionine, phenylalanine, proline, trytophan, tyrosine or valine. This also applies to position 54 which in the wildtype sequence also has a non-polar neutral amino acid.

At position 51, the substituting amino acid may be non-polar and/or basic and/or neutral (in contrast the wildtype amino acid residue which is polar and acidic). Hence, the substituting amino acid may be arginine, asparagine, cysteine, glutamine, lysine etc and is preferably not another polar acidic residue e.g. aspartic acid. Glycine may particularly be used as the substituting amino acid.

At position 52, the substituting amino acid may be non-polar and/or basic and/or acidic and is preferably not a polar neutral amino acid such as asparagine, cysteine (which may lead to disulfide bond problems), glutamine, or threonine. Preferably, the substituting amino acid is a non-polar neutral amino acid, for example, alanine, glycine, isoleucine, leucine, methionine, proline, tyrosine or valine. In a particularly preferred embodiment, the serine residue at position 52 in wildtype streptavidin is substituted by a glycine residue (S52G). Further, in a preferred embodiment, the substituting amino acid residue at position 52 is not any one of the non-naturally occurring residues of L-2-anthrylalanine (antA), β-anthraniloyl-L-α,β-diaminopropionic acid (atnDap) or β-2,6-dansyl-aminophenylalanine (dnsaF).

At position 53, the substituting amino acid may be non-polar and/or neutral and/or acidic. Preferably, the substituting amino acid residue is a polar neutral or polar acidic amino acid residue such as asparagine, aspartic acid, cysteine, glutamic acid, glutamine, serine or threonine. In a particularly preferred embodiment, the substituting residue at position 53 is asparagine (R53N), aspartic acid (R53D) or serine (R53S). In a most preferred aspect, aspartic acid is substituted in place of arginine at position 53 (i.e. R53D).

As discussed previously, any one or more of residues 50 to 54 may be substituted in the mutant streptavidin subunit of the invention.

Particularly the mutant subunit may comprise or consist of a single mutation at any of amino acid positions 50, 51, 52, 53 or 54. More particularly, the mutant subunits may have a single amino acid substitution at position 52 or 53. For example, the mutant subunit of the invention may have a single substitution of glycine for serine at position 52 (S52G) or may have a single substitution of asparagine, aspartic acid or serine for arginine at position 53 (i.e. R53N, R53D or R53S), and preferably R53D.

Further, double, triple or quadruple mutants at positions 50-54 are encompassed by the present invention. Thus, a double mutant may comprise mutations at positions 50 and 51; 50 and 52; 50 and 53; 50 and 54; 51 and 52; 51 and 53; 51 and 54; 52 and 53; 52 and 54; and 53 and 54. In a particularly preferred embodiment, the mutant streptavidin subunit comprises amino acid substitutions at positions 52 and 53. Thus, in this embodiment, a preferred mutant may have a substitution of glycine for serine at position 52 and a substitution of asparagine, aspartic acid or serine for arginine at position 53 i.e. S52G R53N, S52G R53D or S52G R53S. In a particularly preferred embodiment, the double mutant may contain a substitution of glycine for serine at position 52 and a substitution of aspartic acid for arginine at position 53, i.e. S52G R53D.

A triple mutant may comprise amino acid substitutions at for example 50, 51 and 52; 50, 51 and 53; 50, 51 and 54; 51, 52 and 53, 51, 53 and 54 and 52, 53 and 54. A quadruple mutant may comprise amino acid substitutions at 50, 51, 52 and 53; 51, 52, 53 and 54; or 50, 51, 52 and 54. Further, all the residues at positions 50 to 54 may contain amino acid substitutions.

As discussed above, the mutant streptavidin subunit of the invention has a lower off rate for biotin or a biotin conjugate than wildtype streptavidin when the subunit is comprised within streptavidin e.g. assembled into streptavidin or has a lower off rate for biotin than monomeric streptavidin when said mutant is in monomeric form.

The term "off rate" as used herein refers to the rate of dissociation of a ligand from its binding partner. Particularly, the term "off rate" as used herein refers to the rate of dissociation of biotin or a biotin conjugate from streptavidin (or monomeric streptavidin or mutant forms of streptavidin or monomeric streptavidin) and is measured in units of $s^{-1}$. Thus, the smaller the off rate figure, the less biotin is released from the particular streptavidin form over time e.g. per second. The off rate of biotin from wildtype streptavidin is $2.9 \times 10^{-5}$ $s^{-1}$ (Hyre et al., 2000, Protein Sci., 9, 878-885). New figures have been obtained for the off rate of biotin from monomeric streptavidin in the art, namely $3.4 \times 10^{-3}$ $s^{-1}$ and $4.1 \times 10^{-3}$ $s^{-1}$ (Wu and Wong, 2006, Protein Expr. Purif., 46, 268-273).

The off rate of the mutant streptavidin for biotin may be at least 5, 10, 15, 20, 30, 40, 50, 60, 70, 80, 90 or 95% less than the off rate of wildtype streptavidin for biotin ($2.9 \times 10^{-5}$ $s^{-1}$) or a biotin conjugate or the off rate of the mutant streptavidin subunit in monomeric form may be at least 5, 10, 15, 20, 30, 40, 50, 60, 70, 80, 90 or 95% less than the off rate of monomeric streptavidin for biotin or a biotin conjugate. Alternatively viewed, the off rate of the mutant streptavidin for biotin or a biotin conjugate may be at least 2, 3, 4, 5, 6, 7, 8, 9, 10, 20, 30, 40, 50, 60, 70, 80, 90, 100, or 1000 fold lower than the off rate of wildtype streptavidin for biotin or a biotin conjugate or the off rate of the mutant streptavidin subunit when in monomeric form for biotin or a biotin conjugate may be at least 2, 3, 4, 5, 6, 7, 8, 9, 10, 20, 30, 40, 50, 60, 70, 80, 90, 100 or 1000 fold lower than the off rate of monomeric streptavidin for biotin or a biotin conjugate.

The off rate may further be described in terms of the half life in hours for the dissociation of streptavidin from biotin or a biotin conjugate. The half life for conjugated biotin and wildtype streptavidin is approximately 6-100 hours (depending on the conjugate) and the half life of free biotin and wildtype streptavidin is approximately 6.6 hr (Hyre et al, supra). The half life for biotin and monomeric streptavidin is approximately 3 minutes.

Thus the mutant streptavidin subunit of the present invention has a higher half life for biotin (either free or conjugated) than wild type streptavidin when the subunit is assembled into streptavidin or than monomeric streptavidin when the mutant subunit is in monomeric form. The half life of the mutant streptavidin subunit when assembled into streptavidin for biotin conjugates may therefore be at least 7, 8, 9, 10, 15, 20, 30, 40, 50, 60 or 70 hours, or the half life of mutant streptavidin subunit when assembled into streptavidin for free biotin may be at least 7, 8, 9, 10, 15 or 20 hours. Alternatively viewed, the half life of the mutant streptavidin subunit of the present invention is increased by at least 10, 20, 30, 40, 50, 60, 70, 80, 90 or 95% of the half life value of wildtype streptavidin for biotin when the mutant subunit is assembled into streptavidin or monomeric streptavidin for biotin when the mutant subunit is in monomeric form. Further, the half life of the mutant streptavidin subunit may be increased by 2, 3, 4, 5, 6, 7, 8, 9, 10, 20, 30, 40 or 50 fold over the half life of the wildtype streptavidin for biotin when the mutant subunit is assembled into streptavidin or over the half life of monomeric streptavidin for biotin when the mutant is in monomeric form.

The off rate of streptavidin or the streptavidin mutants for biotin can be easily measured using the Biotin-4-fluorescein (B-4-F) off-rate assay described in the Examples. In this assay streptavidin (or a mutant thereof) is incubated with 12 nM B-4-F for 30 minutes at 37° C., where the binding of B-4-F to streptavidin quenches fluorescence. Excess biotin (100 μM) is added and fluorescence is then measured every 10 minutes for 10-18 hours. The rate of recovery of fluorescence indicates B-4-F off-rate from the streptavidin. Thus, the quicker that the fluorescence is seen in the sample the higher is the off rate, as fluorescence only starts to increase once B-4-F has dissociated from streptavidin.

Hence, the off rate of streptavidin from biotin can also be measured in terms of the amount of B-4-F recovered after the 10 hour incubation of the B-4-F off rate assay has been carried out. The amount of B-4-F recovered during an incubation with wildtype streptavidin is at least 9%, for example 10, 11 or 12%. The amount of B-4-F recovered after a 10 hour incubation with a mutant streptavidin of the present invention may be less than 9%, for example less than 8, 7, 6, 5, 4, 3, 2 or 1%. Particularly, the amount of B-4-F recovered may be 2-3%.

The term "biotin" as used herein refers to the molecule whose structure is shown in FIG. 12. Biotin is alternatively known as vitamin H, vitamin B7 and cis-hexahydro-2-oxo H-thieno[3,4] imidazole-4-pentanoic acid. The streptavidin mutant subunits of the present invention are capable of binding to a biotin molecule with a lower off rate than wildtype streptavidin when the mutant subunit is assembled to form streptavidin or with a lower off rate than monomeric streptavidin when the mutant subunit is in monomeric form.

Additionally, the streptavidin mutant subunits of the present invention are capable of binding to a biotin conjugate with a lower off rate than wildtype streptavidin when the mutant subunit is comprised within streptavidin (e.g. assembled to form streptavidin or present within a single chain polypeptide of streptavidin) or than monomeric streptavidin when the mutant subunit is in monomeric form. A biotin conjugate refers to biotin covalently linked to another molecule. Preferably the linkage is through an amide bond or through an ester bond. Thus, biotin may be conjugated to any other molecule or entity, particularly to a nucleic acid, a protein/polypeptide, a fluorophore, a cell, a virus, a bead or to any other surface. For example, biotin may be conjugated to oligonucleotides, oligopeptides, fluorescent molecules, enzymes, organic polymers, carbon nanotubes, small molecule drugs etc. Particularly, the mutant streptavidin subunit of the invention has a lower off rate than wildtype streptavidin when said subunit is assembled into streptavidin or than monomeric streptavidin when the mutant is in monomeric form for biotin conjugates i.e. biotin conjugated to another entity e.g. molecule or cell.

Although, the mutant streptavidin subunits of the invention have a lower off rate for biotin than wildtype streptavidin when said subunit is part of streptavidin or than monomeric streptavidin when the mutant is in monomeric form, it is also possible that the mutant subunits also have a lower off rate for other biotin analogues than wildtype streptavidin when said subunits are part of streptavidin or than monomeric streptavidin when the mutant is in monomeric form. For example, the mutant streptavidin subunits may have a lower off rate than wildtype streptavidin when said subunit is comprised within streptavidin e.g. is assembled to form streptavidin or than monomeric streptavidin when the mutant is in monomeric form for desthiobiotin (also known as dethiobiotin), selenobiotin, oxybiotin, homobiotin, norbiotin, iminobiotin, diaminobiotin, biotin sulfoxide, biotin sulfone, epibiotin, 5-hydroxybiotin, 2-thiobiotin, azabiotin, carbobiotin, methylated derivatives of biotin, and/or ketone biotin. The mutant streptavidin subunits when in tetrameric form may have a lower off rate for these biotin analogues in either free or in conjugated form.

In a particular embodiment however, the mutant streptavidin subunits of the invention may not have a higher stability or off rate than wildtype streptavidin when assembled into or comprised within streptavidin for peptide ligands comprising the amino acid sequence Trp-X-His-Pro-Gln-Phe-Y-Z (SEQ ID NO: 9) in which X represents an arbitrary amino acid and Y and Z either both denote Gly or Y denotes Glu and Z denotes Arg or Lys. In particular, a mutant streptavidin subunit of the invention with a substitution at position 53 may not have a higher stability or off rate than wildtype streptavidin for this peptide ligand when said subunit is assembled into streptavidin.

The mutant streptavidin subunit of the invention may further have other functional properties. Particularly, the on rate of the mutant streptavidin subunit for biotin may be reduced compared to the on rate of wildtype streptavidin for biotin when said subunit is assembled into streptavidin or may be reduced compared to the on rate of monomeric streptavidin for biotin when the mutant is in monomeric form. Hence, the mutant streptavidin subunit of the present invention may associate more slowly with biotin than wildtype streptavidin when said subunit is assembled into streptavidin or than monomeric streptavidin when the mutant is in monomeric form. The on rate of wildtype streptavidin for biotin is known to be approximately $2.0 \times 10^7$ $M^{-1}s^{-1}$. Hence, the on rate of the mutant streptavidin of the present invention may be at least 10, 20, 30, 40, 50, 60, 70, 80 or 90% less than the on rate of wildtype streptavidin of $2.0 \times 10^7 M^{-1}s^{-1}$. Alternatively viewed, the on rate of mutant streptavidin for biotin may be 0.5, 1, 1.5, 2, 2.5, 3, 3.5, 4, 4.5, 5, 10, 20, 30, 40, 50, 60, 70, 80, 90 or 100 fold less than the on rate of wildtype streptavidin of $2.0 \times 10^7$ $M^{-1}s^{-1}$. Particularly, the on rate of the mutant streptavidin may be less than $2.0 \times 10^7$ $M^{-1}s^{-1}$, for example equal or less than $1 \times 10^7 M^{-1}s^{-1}$, $9 \times 10^6 M^{-1}s^{-1}$, $8 \times 10^6 M^{-1}s^{-1}$, $7 \times 10^6 M^{-1}s^{-1}$, $6 \times 10^6 M^{-1}s^{-1}$ or $5 \times 10^6 M^{-1}s^{-1}$.

The on rate can be measured again using an adapted B-4-F assay as described above. Hence, streptavidin or a streptavidin mutant can be incubated with B-4-F for 30 minutes at 37° C. where binding of B-4-F to this protein quenches fluorescence. The on rate can therefore be established by the decrease in the amount of fluorescence which occurs over the incubation time. The faster the rate of decrease in fluorescence, the higher the on rate.

Additionally, the mutant streptavidin of the present invention may have an improved thermostability in comparison to wildtype streptavidin. Streptavidin naturally occurs in tetrameric form i.e. made up of four streptavidin subunits. Streptavidin tetramers will however dissociate into monomeric form at high temperatures. An improved thermostability as used herein hence refers to the ability of mutant streptavidin to retain tetrameric form at a higher temperature than wildtype streptavidin or for a higher percentage of mutant streptavidin molecules to be in tetrameric form at a particular temperature than wildtype streptavidin. For example, thermostability can be measured in terms of the temperature at which 50% of streptavidin is in the tetrameric form and 50% is in the monomeric form i.e. the temperature at which there is 50% dissociation. For wildtype streptavidin, the temperature at which there is 50% dissociation is about 70-75° C. in the absence of biotin. Hence, the mutant streptavidin of the present invention may show 50% dissociation at a higher temperature than 75° C., for example at least 75, 77, 78, 79, 80, 81, 82, 83, 84, 85, 86, 87, 88 89 or 90° C. in the absence of biotin.

Thermostability can be easily determined by heating streptavidin or a mutant thereof to a particular temperature and then placing on ice. The amounts of subunits/tetramers present can be determined using SDS-PAGE and quantifying band intensities.

Particularly, the mutant streptavidin may have enhanced thermostability for biotin conjugate binding which could be widely used in PCR-type applications. Additionally, the mutant streptavidin of the invention may have an enhanced thermostability for biotin conjugate binding which could be widely used in PCR-type applications. An enhanced thermostability for biotin as used herein hence refers to the ability of the mutant streptavidin of the invention to bind to biotin or a biotin conjugate at a higher temperature than wildtype streptavidin or for a higher percentage of the mutant streptavidin of the invention to bind biotin or a biotin conjugate at a particular temperature than wildtype streptavidin. For example, thermostability for biotin or a biotin conjugate can be measured in terms of the temperature at which 50% of the biotin or biotin conjugate is bound by the streptavidin, i.e. the temperature at which there is 50% dissociation. For wildtype streptavidin, the temperature at which there is 50% dissociation is about 50-60° C. For the mutant streptavidin of the present invention, the 50% dissociation point is greater than 70° C., for example greater than 75, 80, 85, or 90° C. Thermostability for biotin or a biotin conjugate can be easily determined by heating streptavidin or a mutant thereof with biotin or a biotin conjugate to a particular temperature and then placing on ice. The amounts of free versus bound biotin conjugate present can be determined using an agarose gel and quantifying the band intensities.

Further, the mutant streptavidin of the invention may have increased mechanical strength than wildtype streptavidin. Hence, the mutant streptavidin of the invention may require a larger unbinding force (pN) to break the bond between itself and biotin than wildtype streptavidin when an equivalent loading rate is used (i.e. when the bond is pulled at the same speed). Thus, the force closely relates and is often linearly proportional to the logarithm of the loading rate (how fast the bond is pulled) and both factors need to be considered when measuring mechanical strength. For example, the mutant streptavidin of the invention may require a force which is at least 10, 15, 20, 25, 30, 35, 40, 45, 50, 55 or 60% larger than that required for wildtype streptavidin to break the bond between itself and biotin at the same loading rate.

The mutant streptavidin or mutant streptavidin subunits of the present invention may be conjugated to other molecules or entities, for example, to a nucleic acid molecule, a protein, peptide, organic compound, inorganic compound, polysaccharide or any combination of these. In particular, the mutant streptavidin or mutant streptavidin subunit may be conjugated to a compound which has a therapeutic or prophylactic effect e.g. an antibiotic, antiviral, vaccine, antitumour agent e.g. a radioactive compound or isotope, cytokines, toxins, oligonucleotides and nucleic acids encoding genes or nucleic acid vaccines. The mutant streptavidin or mutant streptavidin subunit of the invention may further be conjugated to a label, for example, a radiolabel, a fluorescent label, luminescent label, a chromophore label as well as to substances and enzymes which generate a detectable substrate e.g. horse radish peroxidase, luciferase or alkaline phosphatase. Labels for magnetic resonance imaging, PET probes and boron 10 for neutron capture therapy may also be conjugated to the mutant streptavidin or mutant streptavidin subunit of the invention.

In a further embodiment, the invention provides a mutant streptavidin subunit which comprises an amino acid substitution compared to a wildtype streptavidin subunit at one or both of residue positions equivalent to positions 52 and 53 SEQ ID NO. 2 and wherein amino acid residues at positions equivalent to positions 23, 27, 43, 45, 49, 79, 88, 90, 92, 108, 110 and 128 of SEQ ID NO. 2, in said mutant streptavidin subunit, are wildtype, wherein
   (i) when said mutant streptavidin subunit is comprised in streptavidin, said streptavidin has a lower off rate for biotin or for a biotin conjugate than wildtype streptavidin
   or
   (ii) when said mutant streptavidin subunit is in monomeric form said mutant monomeric streptavidin has a lower off rate for biotin or a biotin conjugate than monomeric streptavidin.

A further aspect of the present invention concerns a nucleic acid molecule which comprises a nucleotide sequence encoding a mutant streptavidin subunit of the present invention. Particularly, a nucleic acid molecule which encodes a mutant streptavidin subunit comprising the sequence as set forth in any one of SEQ ID NOs 5-7 is encompassed by the invention.

A vector comprising a nucleic acid molecule of the invention is also provided by the invention. Typically, the nucleic acid molecule may be operably linked to a control sequence present in the vector e.g. a promoter which is capable of providing for the expression of the coding sequence in a host cell. Thus, in addition to the nucleic acid sequence of the invention, the vectors may comprise other elements such as a promoter, enhancer, transcription initiation site, termination site, translation initiation site, polyA site etc. Further the vector may comprise one or more selectable marker genes such as a gene providing for ampicillin resistance or kanamycin resistance. The vector may additionally comprise a signal sequence, allowing exportation of an expressed product outside of the host cell.

The vector is generally selected depending on the intended expression system and may be a transposon, plasmid, virus or phage vector. The vector may be typically introduced into host cells using conventional techniques such as calcium phosphate precipitation, liposomal transfection agents, DEAE-dextran transfection or electroporation.

A further aspect of the present invention concerns a cell which is transformed or transfected with a vector or nucleic acid molecule of the invention. Thus, the cell of the invention may carry at least one copy of a nucleic acid sequence of the invention. The cell may be a prokaryotic cell such as *E. coli* or a eukaryotic cell such as a yeast.

In another aspect of the invention, a process for the production of a mutant streptavidin subunit of the present invention is provided which comprises the following steps:
   a) transforming or transfecting a suitable host cell with a vector which comprises a nucleotide sequence encoding the streptavidin mutant subunit of the invention,
   b) culturing the host cell under conditions which allows expression of the streptavidin mutant subunit to take place, and
   c) isolating the mutant streptavidin subunit.

The subunits may be isolated in monomeric form, e.g. where additional mutations are present preventing tetramerisation or may be isolated in tetrameric form e.g. as mutant streptavidin.

Thus, the mutant streptavidin subunit may be produced using recombinant methodology. It will be understood that the above production process may comprise further steps, such as a step of producing the vector which comprises a nucleotide sequence encoding the streptavidin mutant subunit of the invention. Site directed mutagenesis of a nucleic acid sequence encoding wildtype streptavidin subunit for example may be employed to produce a nucleotide sequence encoding the mutant streptavidin subunits prior to the transformation step (a). Alternatively, the nucleotide sequence encoding the mutant streptavidin subunit may be produced by chemical synthesis. Such a mutated nucleotide sequence may then be ligated into an appropriate vector for host cell transformation or transfection. The host cells transformed or transfected may be any cell as described previously and the vector may be a vector of the present invention.

Alternatively, the mutant streptavidin subunit may be synthesised using standard chemical peptide synthesis techniques. Solid phase synthesis of peptides in which the C-terminal amino acid of the sequence is attached to an insoluble support followed by sequential addition of the remaining amino acids may for example be used.

Once expressed, the mutant streptavidin subunit e.g. in monomeric or tetrameric form may be purified according to standard procedures in the art, including ammonium sulfate precipitation, affinity chromatography, ion exchange chromatography, gel filtration chromatography etc. Particularly, it may be possible to purify the mutant streptavidin subunit using iminobiotin, diaminobiotin or another ligand partner in an affinity column.

It will be understood that after synthesis, expression or purification, the streptavidin subunits (either in streptavidin or in monomeric form) may not be in the conformation of the native protein and thus it may be necessary to denature and reduce the streptavidin and to refold the proteins. Methods which can be used to achieve this effect include denaturing in urea or guanidinium hydrochloride and renaturing by slow dialysis or rapid dilution.

The present invention also provides a kit comprising a mutant streptavidin subunit of the invention. The streptavidin may be conjugated to another molecule as discussed previously or may be coated onto a solid surface such as a plate, column or microspheres. Additionally the kit may comprise biotin and/or biotin analogue(s).

Alternatively, the kit may comprise a nucleic acid molecule comprising a nucleotide sequence encoding a mutant streptavidin subunit of the invention. Hence, the kit may comprise a vector comprising the nucleic acid molecule and/or host cells to allow expression of the molecule after transformation/transfection. Alternatively, the kit may comprise transformed or transfected host cells.

The mutant streptavidin or mutant streptavidin subunit in monomeric form of the invention may be used for any purpose for which wildtype streptavidin or monomeric streptavidin may be used. Thus, the mutant streptavidin or mutant streptavidin subunit in monomeric form may be used for any method involving streptavidin binding to biotin conjugates. The mutant streptavidin or mutant streptavidin subunit of the invention are however particularly useful in methods which require a longer lasting interaction between streptavidin and biotin conjugates in view of their lower off rate for biotin conjugates than wildtype streptavidin or monomeric streptavidin, respectively.

The mutant streptavidin or mutant streptavidin subunit in monomeric form of the present invention may therefore be used in preparative applications where mutant streptavidin or mutant streptavidin subunit in monomeric form immobilised on a solid support is used to capture biotinylated entities e.g. molecules, cells etc which are passed over the solid support. Such biotinylated entities will be stably captured by the mutant streptavidin or the mutant streptavidin subunit in monomeric form on the solid support and may then be detected e.g. by application of a labelled antibody. In this way, it may be possible to purify a biotinylated entity from a composition/solution comprising other entities by virtue of its binding to the mutant streptavidin or mutant streptavidin subunit in monomeric form of the invention.

Thus, the invention provides a method of capturing a biotinylated entity e.g. a molecule, cell, biological complex (one component of which is biotinylated), virus (including bacteriophage), organelle, nanoparticle or other nano-assembly, or liposome comprising the step of passing said biotinylated molecule or cell over an immobilised mutant streptavidin or mutant streptavidin subunit in monomeric form of the present invention.

Further, as discussed above, the invention provides a method of purifying a biotinylated entity from a sample comprising the step of passing said biotinylated entity over an immobilised mutant streptavidin or mutant streptavidin subunit in monomeric form of the invention and discarding the unbound sample.

Additionally, the mutant streptavidin or mutant streptavidin subunit in monomeric form of the present invention may be used in diagnostic methods to bind and detect biotinylated entities e.g. molecules and cells. In such diagnostic assays, typically, the presence of an entity in a sample obtained from a patient may indicate the presence or absence of a condition. For example, some disease conditions may result in the expression of a particular protein which is not usually produced (or is produced in a different amount) in a subject without the condition and which protein can therefore act as a marker for the condition. In order to detect any such markers in a sample obtained from a patient, biotinylated antibodies directed to the marker may be added so that any markers in the sample are biotinylated. Such biotinylated marker proteins may then be captured by mutant streptavidin or mutant streptavidin subunit in monomeric form and detected, where detection may result in the diagnosis of a condition in the patient from whom the sample was obtained.

Thus, biotinylated entities may be captured as described above to an immobilised mutant streptavidin or mutant streptavidin subunit in monomeric form of the invention and may subsequently be detected using a labelled antibody directed to the target entity e.g. by virtue of an ELISA where the detecting antibody may be linked to an enzyme or by immunofluorescence where the antibody may have a fluorescent label, dye or quantum dot. In order to carry out such diagnostic methods, the streptavidin may be immobilised for example to a plate (e.g. to 12, 24, 48 or 96 well plates).

In this respect, a method of detecting a biotinylated entity e.g. molecule or cell is provided comprising the steps of passing the biotinylated entity e.g. molecule or cell over an immobilised mutant streptavidin or mutant streptavidin subunit in monomeric form of the invention and detecting the presence or absence of a bound biotinylated entity using an antibody directed to the molecule or cell.

As discussed above, the detection of a biotinylated molecule or cell in such a method may result in the diagnosis of a condition or disease in a subject.

A particularly preferred use of the mutant streptavidin or mutant streptavidin subunit in monomeric form of the present invention is in cell imaging in view of the low off rate of the mutant streptavidin or mutant streptavidin subunit in monomeric form for biotin. The reduced dissociation of the mutant streptavidin or mutant streptavidin subunit in monomeric form of the invention from biotin conjugates allows the cells labelled with biotin/mutant streptavidin to be visualised for longer than when conventional streptavidin/biotin binding is used. Hence, in this aspect, biotinylated antibodies which are raised against a particular cell surface protein are bound to cells and the mutant streptavidin or mutant streptavidin subunit in monomeric form of the invention is then subsequently added which will bind to the biotin present on the cell surface. The mutant streptavidin or mutant streptavidin subunit in monomeric form used in cell imaging will generally be labelled to allow visualisation of the cells e.g. by immunofluorescence where the mutant streptavidin or mutant streptavidin subunit in monomeric form may be labelled fluorescently e.g. with a fluorophore.

Further, the mutant streptavidin or mutant streptavidin subunit in monomeric form of the invention may be advantageously used in targeting therapeutic agents to tumours. It is possible to label tumour cells using biotinylated antibodies which are directed to tumour cell surface antigens. The mutant streptavidin or mutant streptavidin subunit in monomeric form of the invention conjugated to a therapeutic agent such as a radioactive isotope may then be administered to bind specifically to the biotinylated tumour cells (rather than to normal cells in the body). The mutant streptavidin or mutant streptavidin subunit in monomeric form of the present invention is particularly suited for this use in view of its lower dissociation from biotin than wildtype streptavidin or monomeric streptavidin, respectively. Thus, the mutant streptavidin or mutant streptavidin subunit in monomeric form of the invention will stay bound to the biotinylated tumour cells for longer ensuring that the therapeutic agent is delivered to the tumour cells and that this delivery is specific i.e. there is less dissociation and thus less contact with other normal cells.

The mutant streptavidin or mutant streptavidin subunit in monomeric form of the invention can therefore be used to treat cancer or other diseases which can be treated by the targeted delivery of a therapeutic agent to particular cells. The invention thus provides the mutant streptavidin or mutant streptavidin subunit in monomeric form of the invention conjugated to a therapeutic agent for use in therapy. More particularly, the invention provides the mutant streptavidin or mutant streptavidin subunit in monomeric form of the invention conjugated to a therapeutic agent for treating cancer. As discussed above, the mutant streptavidin or mutant streptavidin subunit in monomeric form in these aspects is used to target a therapeutic agent to a biotinylated cell.

Alternatively viewed, the invention provides a method for treating cancer comprising administering a mutant streptavidin or mutant streptavidin subunit in monomeric form of the invention conjugated to a therapeutic agent to a subject, wherein said subject has been pretreated to label cancerous cells with biotin. As discussed previously, the therapeutic agent may be a radioisotope.

The mutant streptavidin or mutant streptavidin subunit in monomeric form may also be used in vitro to target an agent to which it is conjugated to biotinylated cells.

Further, the mutant streptavidin or mutant streptavidin subunit in monomeric form of the invention can be used in many other applications such as imaging receptor trafficking and using quantum dots where the mutants of the invention e.g. S52G R53D may be more stable in the low pH of endosomes and lysosomes which may promote dissociation in the low pH.

The invention will now be described in more detail in the following non-limiting Examples with reference to the drawings in which:

FIG. 1 shows traptavidin (a mutant streptavidin having S52G R53D mutations in the subunits) as having a lower off-rate.

FIG. 1A shows images of residues mutated to produce traptavidin (S52G R53D) in structures of streptavidin without biotin (1swa) and with biotin (1mk5); protein database structure codes are shown in the parentheses. Biotin is shown as spheres of van der Waals radius. Without biotin the L3/4 loop is disordered and does not give clear electron density.

FIG. 1B shows the off-rate at neutral pH. Avidin, streptavidin and traptavidin bind to biotin-4-fluorescein, quenching its fluorescence. On addition of excess free biotin, biotin-4-fluorescein dissociates and the increase in fluorescence is observed at 37° C. and pH 7.4. Mean of triplicate measurements ±1 s.d.

FIG. 1C shows the off-rate at pH 5 of biotin-4-fluorescein from streptavidin or traptavidin at 37° C. Means of triplicate measurements ±1 s.d are shown.

FIG. 2 shows traptavidin as having a lower on-rate. Streptavidin (top graph) or traptavidin (bottom graph) were incubated with biotin-4-fluorescein at 37° C. and the rate of fluorescence quenching upon binding was measured. Mean of triplicate measurements ±1 s.d.

FIG. 3 shows the interaction of the 4 streptavidin subunits and the provision of Trp 120 in an adjacent subunit to the biotin binding site of a subunit. The streptavidin tetramer (from Protein Data Bank 1 swe) is shown in cartoon format, except for each Trp120 in stick format and each biotin shown in van der Waals sphere format.

FIG. 4 shows traptavidin as having increased thermostability. (A) Thermo stability of the tetramer structure. Streptavidin (upper panel) or traptavidin (middle panel) were incubated at the indicated temperatures for 3 min before SDS-PAGE followed by Coomassie staining. The positive control (c) was mixed with SDS prior to heating at 95° C. Tetramer and monomer bands are indicated. In FIG. 4B (upper), the percentage monomer from duplicate gels is plotted.

FIG. 4B (lower panel) shows the thermostability of biotin-conjugate binding. Streptavidin or traptavidin were incubated with biotinylated DNA and heated at the indicated temperature for 3 min before agarose gel electrophoresis and imaging of DNA. The left lane is a control with no streptavidin or traptavidin added. Bands corresponding to DNA free or bound to streptavidin or traptavidin are marked. Under each lane the percentage of biotinylated DNA free from streptavidin or traptavidin is labeled.

FIG. 5 shows that traptavidin shows high specificity for cellular imaging with a strong signal on AP-IGF1R/BirA-ER expressing mammalian cells and minimal binding to equivalently treated cells when traptavidin was pre-blocked with free biotin. The staining with traptavidin and streptavidin (each conjugated to Alexa Fluor 555, left column) was comparable. Histone H2B fused to enhanced cyan fluorescent protein (H2B-ECFP, right column) is a nuclear co-transfection marker FIG. 6 shows that traptavidin has increased mechanical stability.

FIG. 6A shows a system for AFM measurement of streptavidin/traptavidin mechanical stability (not to scale).
B shows mechanical strength of traptavidin at the single molecule level, using dynamic force spectroscopy with an atomic force microscope (AFM). A cantilever coated with streptavidin or traptavidin was pulled away from a biotinylated bead attached to a surface. AFM showed that traptavidin had significantly greater mechanical stability than streptavidin to a biotinylated ligand over a range of loading rates. Means are shown ±1 s.e.m. (streptavidin n=400, traptavidin n=562), with a line of best fit (solid) and 95% confidence limits to this line (dashed).

FIG. 7 shows that traptavidin resists molecular motor translocation.

FIG. 7C shows that traptavidin is displaced by FtsK50C less than streptavidin. Displacement of streptavidin/traptavidin by FtsK50C was determined by agarose gel electrophoresis, with fluorescent visualization of DNA. FtsK50C dissociates from DNA upon electrophoresis but bound streptavidin/traptavidin causes the gel shift indicated with arrows. Controls are shown without streptavidin/traptavidin and without ATP, preventing FtsK50C activity. % free DNA and % DNA displaced by FtsK50C for duplicate assays are indicated under each lane.

Figure 1A:
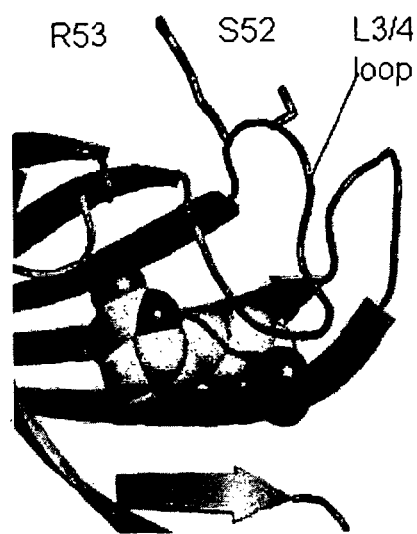
Figure 1A:
Figure 1B:
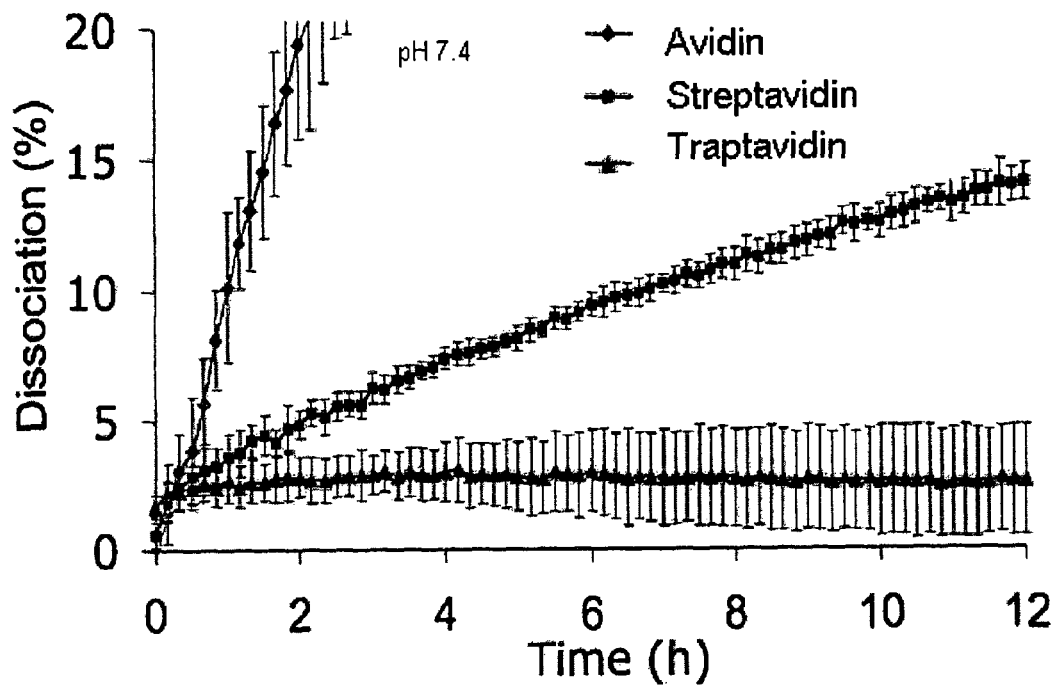
Figure 1C:
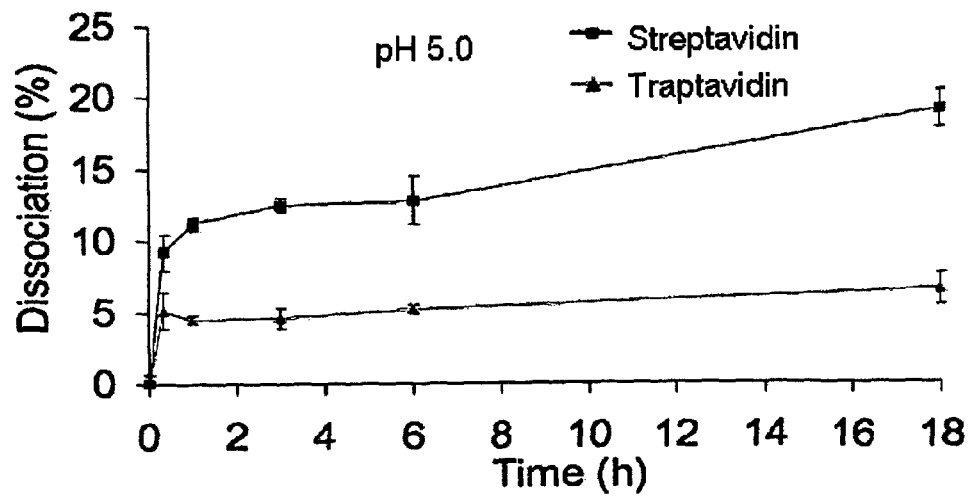
Figure 8:
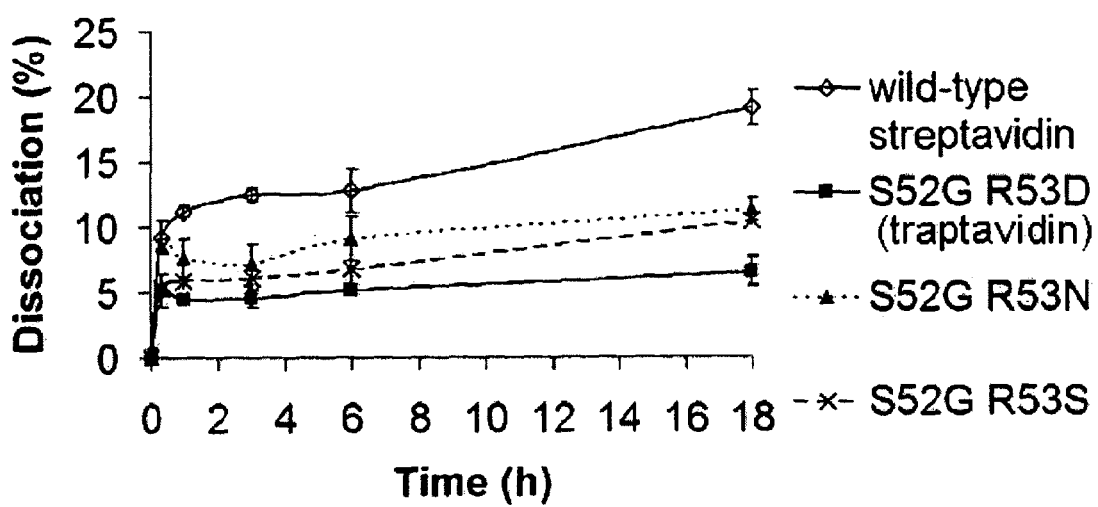

FIG. 8 shows the off-rate at pH 5 and 37° C. of biotin-4-fluorescein from S52G R53S and S52G R53N mutants of streptavidin, relative to wild-type streptavidin or traptavidin (S52G R53D) as was shown in FIG. 1C. Means of triplicate measurements ±1 s.d are shown.

FIG. 9 shows SEQ ID NO. 1, the full length sequence of streptavidin subunit, before signal peptide cleavage.

FIG. 10 shows SEQ ID NO.2, the mature streptavidin subunit sequence.

FIG. 11A shows SEQ ID NO. 3, the core streptavidin subunit sequence and FIG. 11B shows the core streptavidin subunit sequence with a C-terminal His tag (6His).

FIG. 12 shows the structure of biotin where pKa is about 4 so $-CO_2^-$ group is nearly all deprotonated at neutral pH.

FIG. 13A shows SEQ ID NO. 5, the sequence of a mutant streptavidin subunit having S52G R53D and FIG. 13B shows SEQ ID NO. 5 with C-terminal 6His.

FIG. 14 shows SEQ ID NO. 6, the sequence of a mutant streptavidin subunit having S52G R53S. This sequence can also be used with a C-terminal 6His FIG. 15 shows SEQ ID NO. 7, the sequence of a mutant streptavidin subunit having S52G R53N. This sequence can also be used with a C-terminal 6His.

EXAMPLE 1

Materials and Methods
General

Figure 7A:
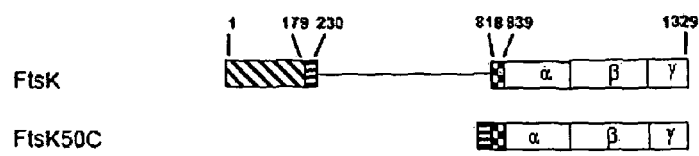
FIG. 7A shows domain organisation of the bacterial protein FtsK, a powerful motor involved in chromosome segregation, and the soluble FtsK50C construct used here.
Figure 7A:
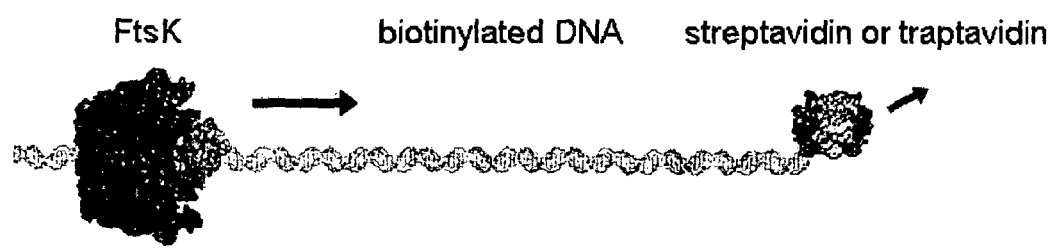
Figure 7B:
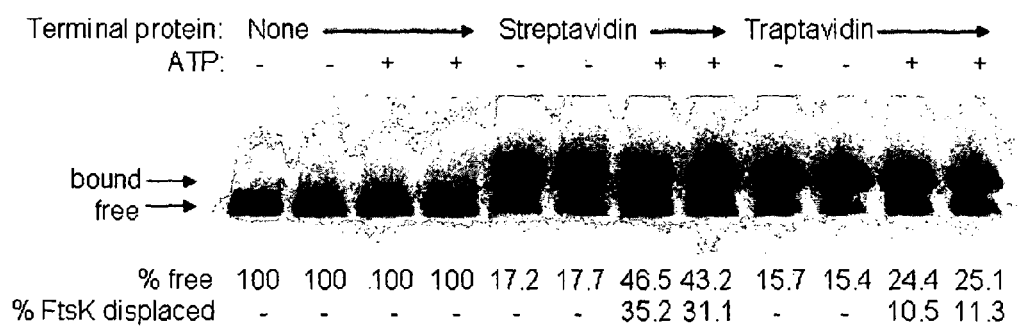
FIG. 7B shows a cartoon of the FtsK assay: DNA, containing a loading site for FtsK50C and a terminal biotin, was capped with traptavidin or streptavidin. In the presence of ATP, FtsK50C translocates along the DNA and collides with streptavidin/traptavidin.

Biotin (Sigma) was dissolved in DMSO at 100 mM. Avidin (Sigma) was dissolved in PBS at 23 µM. SDS-PAGE was performed at 200 V with the gel box (X Cell SureLock, Invitrogen) surrounded by ice to prevent dissociation of the streptavidin subunits during electrophoresis. Structures of streptavidin without biotin (1swa) (Freitag et al., 1997, Protein Sci., 6, 1157-1166) and with biotin (1mk5) (Hyre et al., 2006, Protein Sci., 15, 459-467) were displayed using PyMOL (DeLano Scientific). FIG. 7B was constructed with PyMOL based on 1swe (Freitag et al., 1997, supra), 2iuu (Massey et al., 2006, Mol. Cell, 23, 457-469) and 2ve9 (Lowe et al., 2008, Mol. Cell, 31, 498-509).

Plasmid Construction $His_6^{-ve}$ streptavidin refers to core streptavidin (Sano et al., 1995, J. Biol. Chem., 270, 28204-28209) with no $His_6$ tag in pET21a(+) (Novagen). Core streptavidin (Sano et al., 1995, supra) with $His_6$ at the C-terminus in pET21a(+) (Howarth et al., 2006) was otherwise used. Traptavidin was generated by introducing the S52G R53D mutation into Streptavidin (with a $His_6$ tag) by QuikChange™ (Stratagene) using the following primer and its reverse complement: 5'GAATCCGCTGT-TGGTAACGCTGAAGGCGATTACGTTCT-GACCGGTCGT TAC (SEQ ID NO: 10). S52G R53S and S52G R53N were produced by an equivalent method. The mutations were confirmed by DNA sequencing. AP-IGF1R was constructed from pcDNA3 containing human IGF1R (a kind gift from Val Macaulay, University of Oxford) by PCR of two fragments, the first fragment with 5'CAAC GCTAGCGCCGCCACCATG (SEQ ID NO: 11) and 5'CACTCGATCTTCTGGGCCTCGAA-GATATCGTTCAGGCCGCCAATCTCTC CACTCGTCG-GCCAGAG (SEQ ID NO: 12) and the second fragment with 5'GAGGCCCAGAAGATCGAGTGGCAC-GAGGGCAGTGAAGGATCTGCGGA AATCTGCGGGC-CAGGC (SEQ ID NO: 13) and 5'GATTGCGGCCGCTCAG-CAGGTC (SEQ ID NO: 14). The fragments were joined by overlap extension PCR, digested with NheI and NotI and ligated into pcDNA3.1. The acceptor peptide (GLN-DIFEAQKIEWHE; SEQ ID NO: 15) was thus inserted after the IGF1R signal sequence along with a 6 amino acid spacer before the start of the N-terminus of mature IGF1R. BirA-ER and pECFP-H2B (human histone H2B fused to enhanced cyan fluorescent protein) have been previously described (Howarth and Ting, 2008, Nat. Protoc., 3, 534-545).

Streptavidin/Traptavidin Expression and Purification

An overnight culture of streptavidin, S52G R53N streptavidin, S52G R53S streptavidin, or traptavidin, picked from a freshly grown colony of E. coli BL21 (DE3) RIPL (Stratagene), was diluted 100-fold into LB ampicillin, grown to $OD_{600}$ 0.9 at 37° C., induced with 0.5 mM IPTG, and incubated for a further 4 hr at 37° C. Inclusion bodies were isolated from the cell pellet by incubation with 10 mL 300 mM NaCl, 50 mM Tris, 5 mM EDTA, 0.8 mg/mL lysozyme, 1% Triton X-100 pH 7.8 for 30 min at 25° C. followed by 9 min pulsed sonication on ice at 40% amplitude on a Sonics Vibra-Cell sonicator. Following centrifugation at 27,000 g for 15 min, the inclusion body pellet was washed three times in 10 mL 100 mM NaCl, 50 mM Tris, 0.5% Triton X-100 pH 7.8 and then dissolved in 6 M guanidinium hydrochloride pH 1.5 (GuHCl). Protein in GuHCl was refolded by rapid dilution into PBS at 4° C. and stirring overnight (Howarth and Ting, 2008). Ni-NTA resin (Qiagen), equilibriated in 300 mM NaCl, 50 mM Tris, 10 mM imidazole pH 7.8, was added and rotated overnight at 4° C. The next day, the resin was isolated by centrifugation, washed once with 5 mL 300 mM NaCl, 50 mM Tris, 30 mM imidazole pH 7.8 and then added to a poly-prep column (Bio-rad) for elution with 5 mL 300 mM NaCl, 50 mM Tris, 200 mM imidazole pH 7.8. The eluate was dialyzed three times against PBS. $His_6^{-ve}$ streptavidin was expressed and purified as described (Howarth et al., 2006, Nat Methods, 3, 267-273). Protein concentration was determined in PBS from $OD_{280}$ using $\epsilon_{280}$ of 34,000 $M^{-1}cm^{-1}$. (Sano and Cantor, 1990, Proc. Natl. Acad. Sci. USA, 87, 142-146). Typical yields were 8 mg/L of culture for streptavidin and 5 mg/L culture for traptavidin.

Off-Rate Assay

The off-rate of biotin-4-fluorescein from avidin, streptavidin or traptavidin was measured using a PHERAstar platereader with 480 nm excitation and 520 nm emission (BMG LABTECH). In this assay the binding of biotin-4-fluorescein to an excess of binding protein results in quenching of fluorescein emission (Kada et al., 1999, Biochim. Biophys. Acta, 1427, 33-43). As the biotin-4-fluorescein dissociates, the fluorescence recovers. The assay was performed in the presence of excess biotin so that sites left open by biotin-4-fluorescein dissociation are immediately re-filled by biotin. 1 µM protein in 10 µL PBS was added to 12 nM biotin-4-fluorescein (Invitrogen), 0.12 mg/mL BSA in 170 µL PBS and incubated for 1 hr at 37° C. 20 µL PBS or 20 µL 1 mM biotin in PBS was then added and fluorescence measurements immediately started at 37° C. Percentage dissociation was calculated as (signal with biotin−signal without biotin)/(signal without quenching−signal without biotin)×100.

Since biotin-4-fluorescein fluorescence is decreased at low pH, 100 nM streptavidin, S52G R53N streptavidin, S52G R53S streptavidin, or traptavidin was incubated with 12 nM biotin-4-fluorescein in 100 mM NaCl, 30 mM sodium citrate pH 5.0 for 3 hr at 25° C., before incubating at 37° C. and adding 100 µM biotin and incubating for various times. Samples were then placed on ice to block further dissociation, adjusted to pH 7.2 with 1M HEPES pH 8.3, and fluorescence intensity was immediately measured as above. p-values were calculated using two-tailed Student t-tests from the data at the final timepoint.

On-Rate Assay

The on-rate of biotin-4-fluorescein from streptavidin or traptavidin was measured in PBS on a PHERAstar platereader (BMG LABTECH). In this assay the binding of biotin-4-fluorescein to streptavidin/traptavidin results in quenching of the fluorescein emission (Kada et al., 1999). 20 µL 10 nM streptavidin or traptavidin was added to 180 µL 56 µM biotin-4-fluorescein and the fluorescein emission at measured every 6 s at 25° C. The concentration of free biotin-4-fluorescein was calculated as (signal with biotin−signal without biotin)/ (signal without quenching−signal without biotin)×50 µM starting biotin-4-fluorescein. Linear regression using Graph-Pad Prism was applied to the plot of ln free biotin-4-fluorescein against time, with the gradient equal to $k_{on}$×[streptavidin or traptavidin].

Thermostability Assay

3 µM streptavidin or traptavidin in PBS was heated at the indicated temperature for 3 min in a Bio-Rad DNA Engine® Peltier Thermal Cycler and then immediately placed on ice (Bayer et al., 1996, Electrophoresis, 17, 1319-1324). Samples were mixed with 6×SDS-PAGE loading buffer and loaded onto a 18% polyacrylamide gel. The 100% monomer positive control was mixed with SDS loading buffer prior to heating at 95° C. for 3 min. Band intensities were quantified using a ChemiDoc XRS imager and QuantityOne 4.6 software (Bio-Rad).

To determine the thermostability of bioin-conjugate binding, 5.0 μM streptavidin or traptavidin in PBS was incubated with 21 nM monobiotinylated DNA in 4 μL for 30 minutes at 25° C. The samples were made up to a total volume of 10 μL with a final concentration of 100 μM biotin, 20 mM Tris acetate, 1 mM DDT, 2 mM magnesium acetate and 20 mM potassium glutamate pH 7.5 and were incubated for 5 minutes at 25° C. Samples were then heated at the indicated temperature for 3 minutes using a Thermal Cycler and cooled to 10° C. An agarose gel of 1.5% was run at 6.0V/cm in TAE at 25° C. for 45 minutes and DNA stained with ethidium bromide was visualized using a ChemiDoc XRS imager and QuantityOne 4.6 software. The percentages were calculated as 100× the intensity of the band for free DNA divided by the summed intensities of the bands for free and bound DNA. The 439 bp biotinylated DNA was prepared by PCR using Taq polymerase employing the primers Fts1 and the internally biotinylated primer bioFts2 (Eurofins) from the plasmid pJEG41-N1.

Fluorophore Conjugation

Streptavidin and traptavidin were labeled with Alexa Fluor 555 by adding 1/10 volume of 1 M NaHCO$_3$ pH 8.3 and then a 10-fold molar excess of Alexa Fluor 555 succinimidyl ester (Invitrogen) (stock dissolved at 1 mg/mL in dry dimethylformamide) and incubating for 4 hr at room temperature. Free dye was separated using 1 mL packed volume Sephadex G-25 (Sigma) in a poly-prep column. Fractions containing labelled protein were pooled and dye was further removed by three rounds of dialysis in PBS.

Cell Culture, Biotinylation and Imaging

COST cells were grown in DMEM with 10% Fetal Calf Serum, 50 U/mL penicillin and 50 μg/mL streptomycin. Cells were transfected using Lipofectamine 2000 (Invitrogen) following manufacturer's instructions with 0.25 μg AP-IGF1R, 0.2 μg BirA-ER and 0.05 μg H2B-ECFP per well of a 48 well plate. Cells were incubated with 10 μM biotin overnight for optimum biotinylation by BirA-ER. On the next day, cells were washed 3× in PBS with 5 mM MgCl$_2$ (PBS/Mg) and kept thereafter at 4° C. Cells were incubated for 15 min in PBS/Mg with 1% dialyzed BSA and 0.4 μM Alexa Fluor 555 conjugated traptavidin. Cells were washed with PBS/Mg 3× before imaging live. Cells were imaged using a wide-field DeltaVision Core fluorescent microscope (AppliedPrecision) with a 40× oil-immersion lens. ECFP (436DF20 excitation, 480DF40 emission, Chroma 86002v1 dichroic), Alexa Fluor 555 (540D420 excitation, 600DF50 emission, Chroma 84100bs polychroic), and bright-field images were collected and analyzed using softWoRx 3.6.2 software. Typical exposure times were 0.1-1.0 s and fluorescence images were background-corrected. Different samples in the same experiment were prepared, imaged and analyzed under identical conditions.

AFM

AFM cantilevers (Veeco MLCT-AUHW) with a nominal spring constant of 0.01 N/m were used in all measurements and calibrated by the thermal fluctuation method (Hutter and Bechhoefer, 1993, Review of Scientific Instruments, 64, 1868-1873). Cantilevers were briefly washed in acetone and then UV irradiated for 15 minutes. Cantilevers were then briefly dipped in 0.1M NaHCO$_3$ pH 9.0, air-dried, and coated in 0.5 mg/mL biotinamidocaproyl-Bovine Serum Albumin (biotin-BSA) (Sigma) overnight at 4° C. in a humidified chamber. Cantilevers were washed three times in PBS and then coated with 0.01-0.3 mg/mL streptavidin or traptavidin for 15 mins at 25° C. 35 mm$^2$ dishes were coated with 0.1M NaHCO$_3$ pH 9 and then 0.5 mg/mL non-recombinant streptavidin (from *Streptomyces avidinii*, Pierce) in 0.1M NaHCO$_3$ pH 9 overnight in a humidified chamber at 4° C. Biotinylated agarose beads (Sigma) were aspirated onto the dish.

Measurements were conducted at 25° C. with a custom built AFM (Rico and Moy, 2007, J. Mol. Recogniti., 20, 495-501). Functionalized cantilevers were pressed against the agarose beads and the cantilever was retracted from the bead at 374-532 nm/s. So that in most cases only 0 or 1 bond formed between the cantilever and the bead, the beads were indented with a minimal amount of force of 25-50 pN and 2.5 μg/mL biotin-BSA was added to titrate the binding sites on the cantilever to achieve 30-40% adhesion frequency. Single molecule rupture forces were determined by calculating the force in the retraction trace at the initial point of rupture, using Igor Pro 6.04 (Wavemetrics Inc.). Forces were corrected with the hydrodynamic drag force (Alcaraz et al., 2002, Langmuir, 18, 716-721). The loading rate was determined as the slope of the force vs time plot before the rupturing of the single molecule bond and significance was evaluated with the Mann-Whitney test.

FtsK Assay

A 597 bp monobiotinylated DNA fragment, containing two 8 bp KOPS loading sites 130 bp from the biotinylated end, was generated by PCR with Taq polymerase using primers 5'-CGGAGACGGTCACAGCTTG (SEQ ID NO: 16) and 5'-[Btn]CGGCTCGTATGTTGTGTGG (SEQ ID NO: 17) (Sigma-Genosys) from plasmid pJEG41, a derivative of pUC18 with a lambda phage insert. *E. coli* FtsK50C, a soluble fragment containing the α, β and γ domains of FtsK (FIG. 7A), was purified as described (Löwe et al., 2008, Mol. Cell, 31, 498-509). The FtsK displacement assay was performed at 25° C. in 25 mM Tris pH 7.5, 10 mM MgCl$_2$. 5.9 nM DNA fragment was incubated with 0.5 μM streptavidin or traptavidin for 15 min, followed by 100 μM biotin to block free biotin binding sites. 1 μM FtsK50C was added and allowed to bind to the DNA for 5 min. 2.5 mM ATP was added to start the reaction, which was stopped after 2 min with 0.1% SDS and 20 mM EDTA. Samples were incubated for 20 mM to allow FtsK50C denaturation, mixed with 10× gel loading buffer (250 mM Tris pH 7.5, 20 mM EDTA, 50% glycerol, 2.5% bromophenol blue) and loaded on a 1.5% agarose gel in 1×TBE (89 mM Tris, 89 mM boric acid, 2 mM EDTA, pH 8.3) at 10 V/cm for 2 hr at 25° C. Gels were stained with SYBR Green (Invitrogen) for 2 hr, washed in ddH$_2$O for 30 mM, imaged using a Fuji FLA3000 scanner, and quantified using Image Gauge software (Fuji). p-values were calculated using a two-tailed Student t-test.

Results

Traptavidin Shows Negligible Off-Rate from Biotin Conjugates

The S52G R53D mutant of streptavidin (FIG. 1A) was termed traptavidin. Traptavidin gave comparable expression yields to wild-type streptavidin and showed a dramatically reduced biotin conjugate off-rate (FIG. 1B, p=0.0008). The biotin-4-fluorescein dissociation assay was performed under stringent conditions, at 37° C. in the presence of a large excess of competing free biotin, and yet after the ~2% change at the initial time-point, there was very little dissociation from traptavidin over the subsequent 12 hr. In contrast, streptavidin dissociated steadily over the assay, while avidin dissociated very much faster than streptavidin, as previously observed (Nordlund et al., 2005, supra).

Since streptavidin stability is limiting when labelling proteins that recycle through the endosomal compartment (Bruneau et al., 2005, J. Neurosci., 25, 9949-9959), the off-rate at pH 5 was also assessed. Dissociation was faster than at neutral pH, and again there was an initial burst of dissociation but traptavidin dissociation was significantly slower than streptavidin (p=0.0018).

Traptavidin has a Reduced on-Rate

Figure 2:
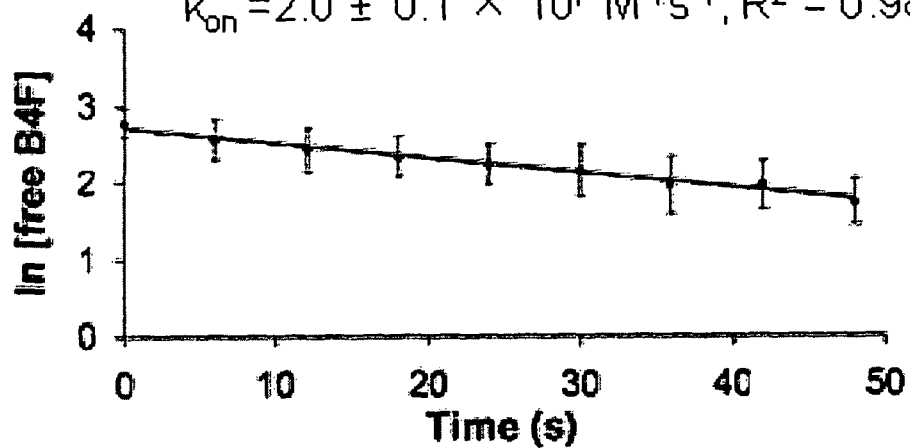
Figure 2:
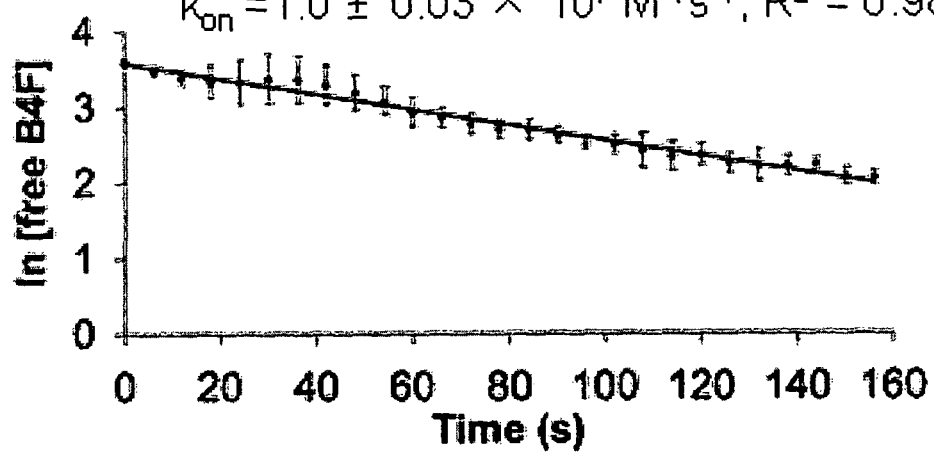
Figure 3:
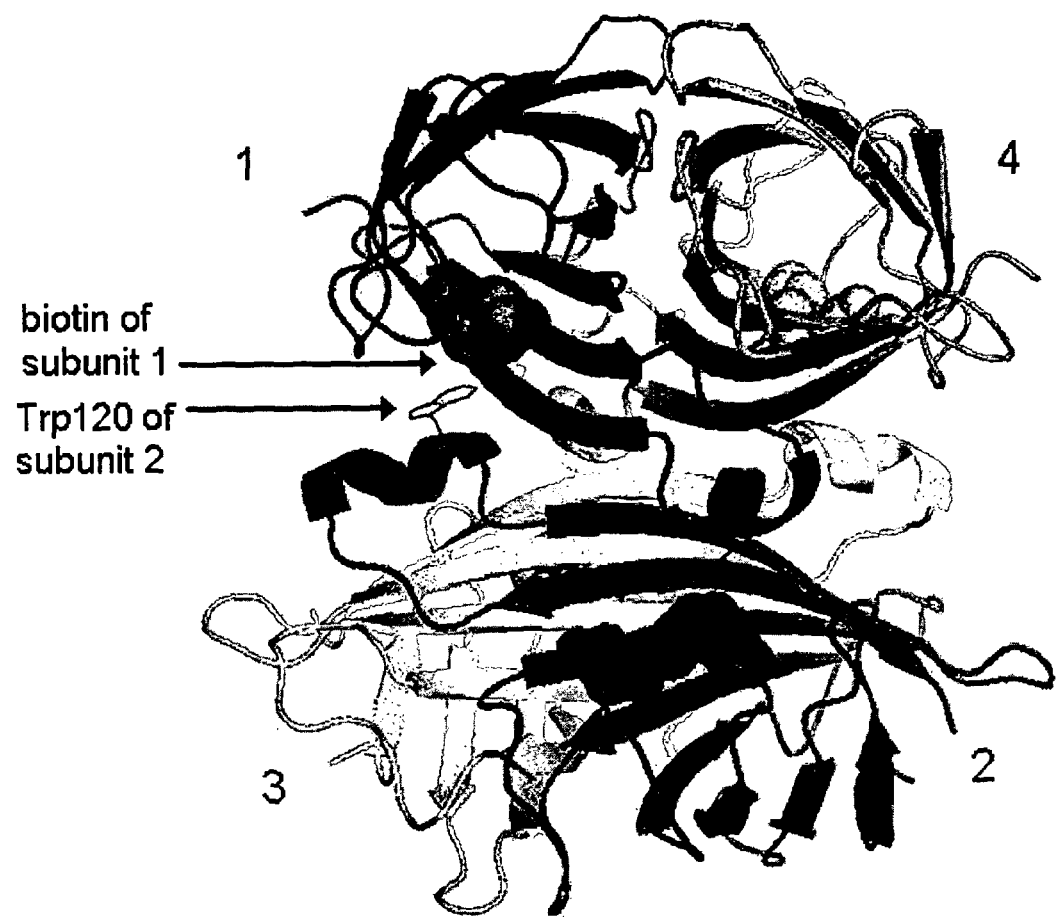

The biotin conjugate on-rate was determined based on the speed of biotin-4-fluorescein quenching. The on-rate of traptavidin was reduced approximately 2-fold relative to streptavidin (FIG. 2).

Traptavidin has Improved Thermostability

Figure 4A:
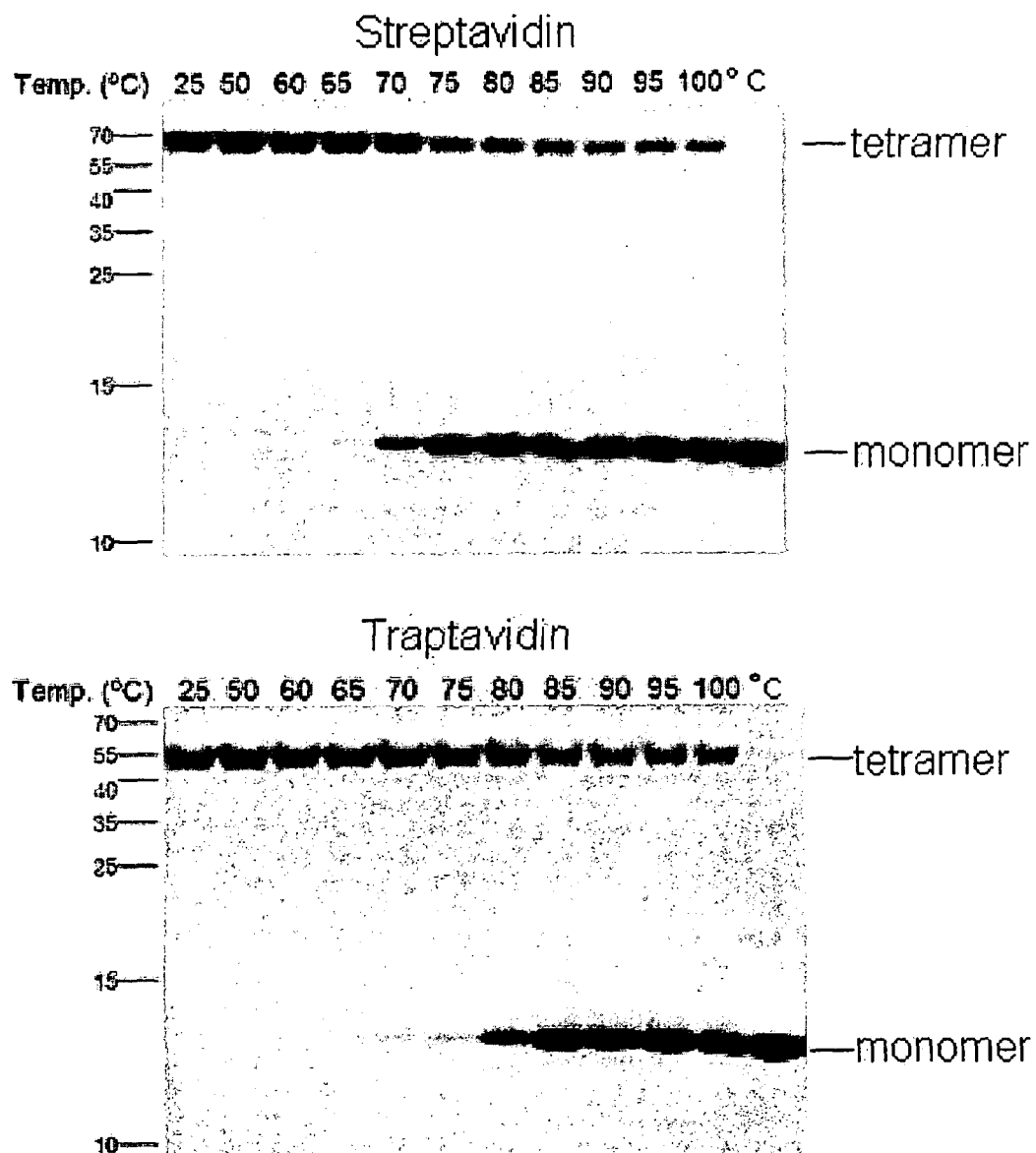
Figure 4B:
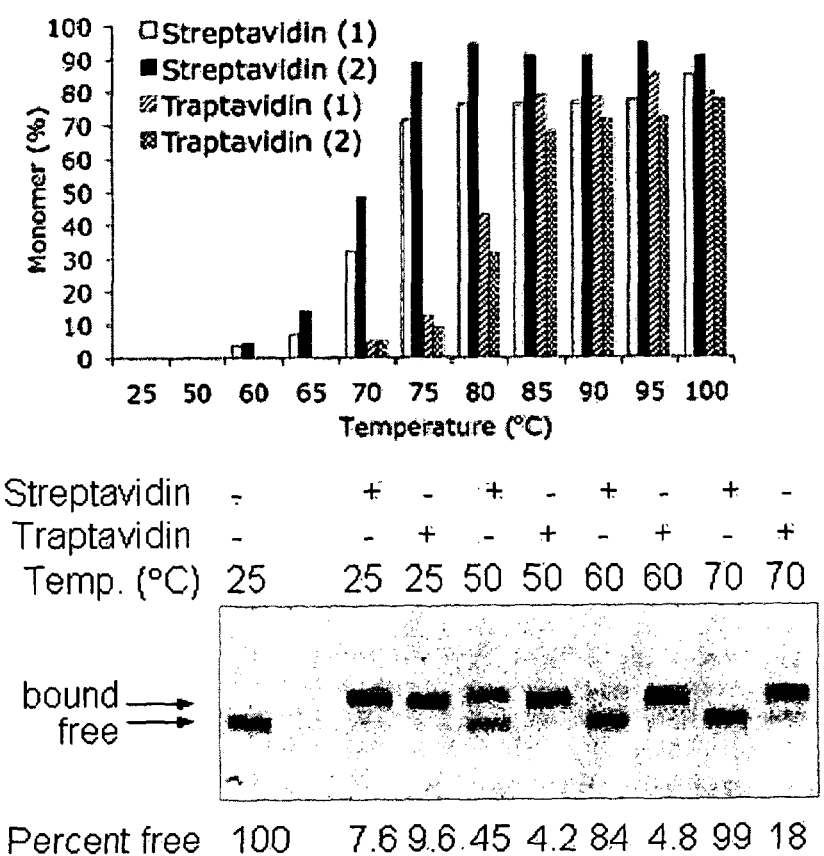

Streptavidin can be used in assays at high temperature, such as PCR. Many mutations in streptavidin, even distant from the subunit interface, can reduce tetramer stability (Qureshi et al., 2001, J. Biol. Chem., 276, 46422-46428; Wu and Wong, 2005, J. Biol. Chem., 280, 23225-23231). Streptavidin and traptavidin were incubated at a range of temperatures and dissociation into subunits was assessed by SDS-PAGE (FIG. 4). Traptavidin had increased thermostability (50% dissociation for traptavidin ~85° C. and for streptavidin ~75° C.). Biotin conjugate binding stability was determined at increased temperatures (FIG. 4B). There was complete dissociation of biotinylated DNA from streptavidin at 70° C. but at this temperature most ligand was still bound to traptavidin. Thus for applications requiring thermal stability, traptavidin could prove superior to streptavidin.

Traptavidin for Cellular Imaging

Figure 5:
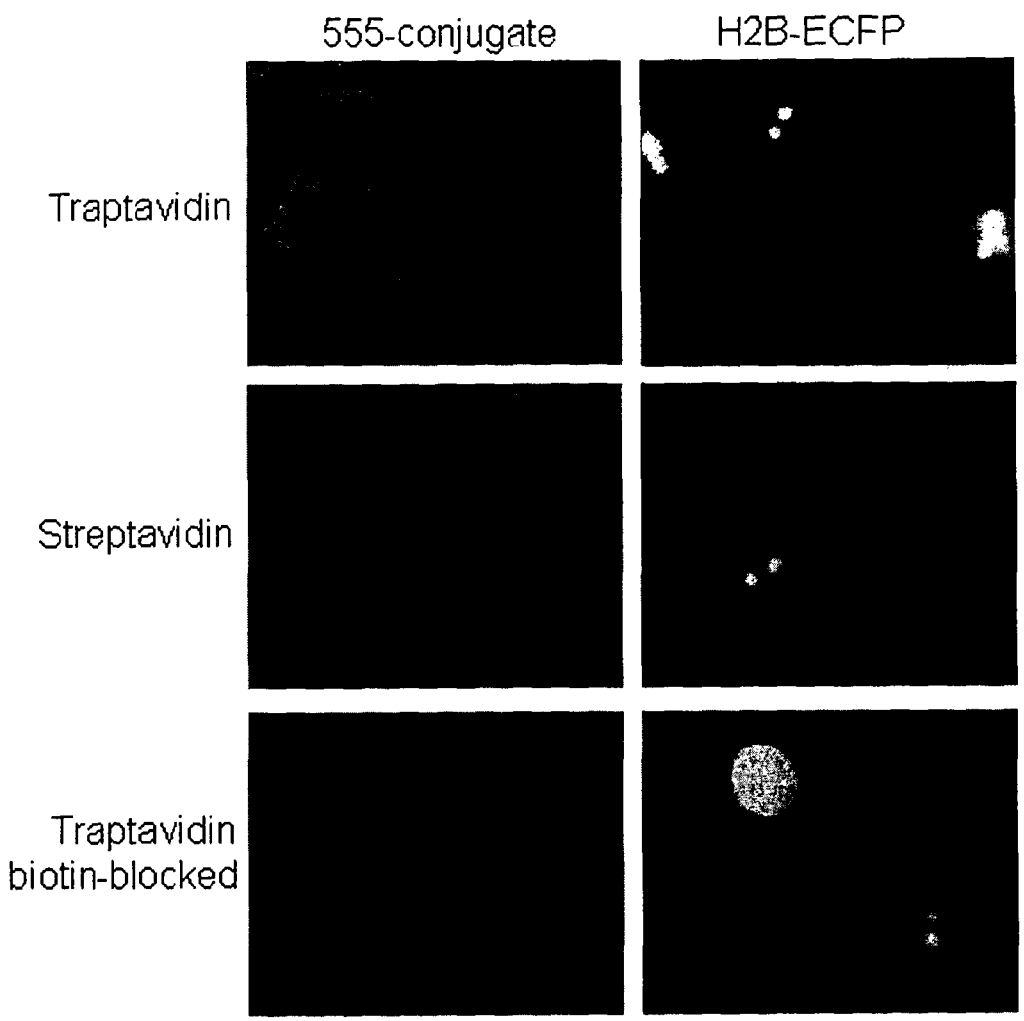

Imaging of cell surface proteins using biotin ligase and streptavidin has the advantages that the protein needs only to be modified with a 15 amino acid tag and labelling is rapid and sensitive (Howarth and Ting, 2008, Nat. Protoc., 3, 534-545). The slower off-rate of traptavidin could be advantageous for biotin ligase-dependent imaging but changes in surface charge can affect non-specific cellular binding, as seen for avidin compared to its lower pI mutants (Marttila et al., 2000, FEBS Letters, 467, 31-36). Hence it was investigated whether traptavidin showed similar specificity to streptavidin on mammalian cells. The type 1 insulin-like growth factor receptor (IGF 1R) is an important regulator of cell survival and is a target of growing importance in cancer therapy. IGF1R was genetically fused to the acceptor peptide tag (AP-IGF1R), expressed in COS7 cells, biotinylated with co-expressed biotin ligase (BirA-ER), and detected with fluorescent traptavidin or streptavidin (FIG. 5). Traptavidin showed high specificity for cellular imaging, with a strong signal on AP-IGF1R/BirA-ER expressing cells and no detectable binding to untransfected neighboring cells expressing only AP-IGF1R.

Traptavidin Binding to Biotin Conjugates has Increased Mechanical Strength

Figure 6A:
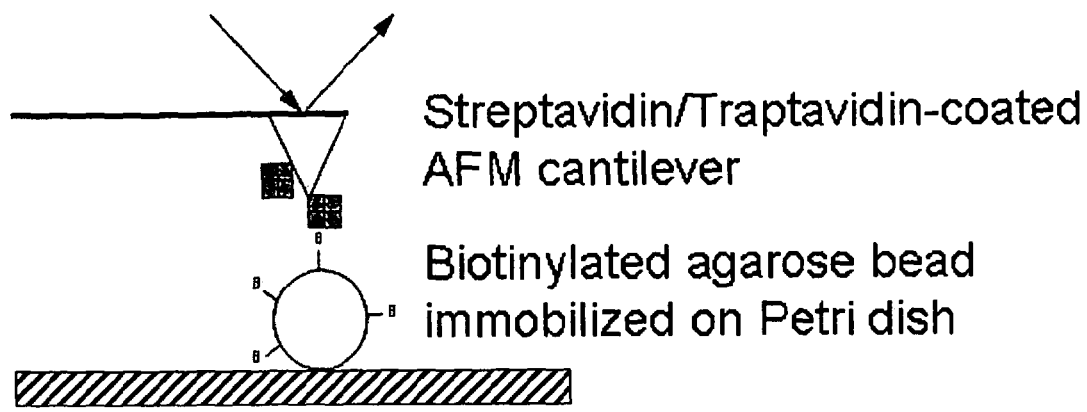
Figure 6B:
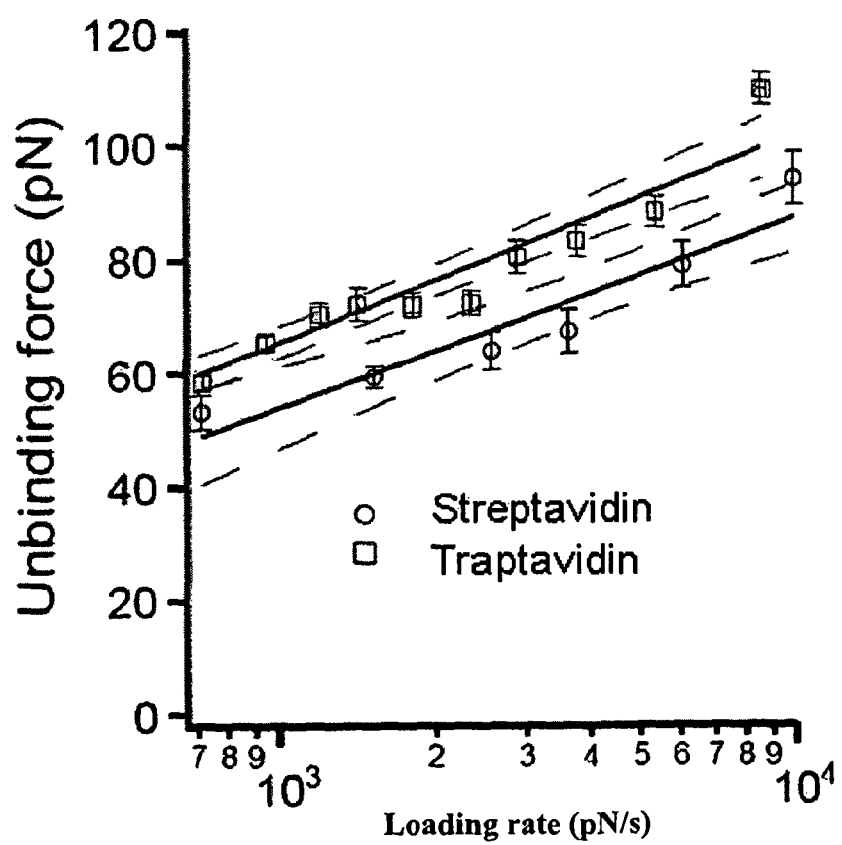

The relationship for proteins between bond stability over time and bond resistance to applied forces is complex, including surprising behaviours such as latch bonds and bonds that mature over time (Evans and Calderwood, 2007, Science, 316, 1148-1153). Applying a force changes the activation energy height and landscape for bond dissociation. The mechanical strength of traptavidin was probed at the single molecule level by force spectroscopy using an atomic force microscope (AFM). Here a cantilever coated with streptavidin or traptavidin was pulled away from a biotinylated bead attached to a surface (FIG. 6A). Rupture forces are not constant but depend upon the rate at which the force is loaded onto the bond, so the force to break an individual bond from the biotin conjugate to streptavidin/traptavidin was characterized over the range 0.3-3 nN/s. This showed that traptavidin has significantly greater mechanical stability than streptavidin to a biotinylated ligand (FIG. 6B)

Traptavidin can Resist the Molecular Motor FtsK

FtsK loads on to DNA preferentially at 8 base pair sequences known as KOPS sites, and proceeds directionally along DNA (Bigot et al., 2005, EMBO J., 24, 3770-3780). A soluble and catalytically active fragment of FtsK, called FtsK50C (FIG. 7A) was used. A short piece of DNA was constructed containing one KOPS site, so that FtsK50C would load onto the DNA and then translocate until encountering streptavidin/traptavidin, linked to a biotinylated nucleotide at the end of the DNA (FIG. 7B). If FtsK50C induced streptavidin/traptavidin dissociation, this would cause a mobility shift upon electrophoresis. Despite the strength of the streptavidin-biotin interaction, FtsK50C translocation, in the presence of ATP, was able to dissociate 33% of streptavidin from the DNA in 2 min, whereas for traptavidin only 11% dissociated (p=0.0087) (FIG. 7C). Incubation for 15 min did not result in any further displacement by FtsK (data not shown). This assay provides additional evidence for the increased mechanical strength of the traptavidin-biotin interaction. This method also provides a new approach to investigate the high forces generated by FtsK as it translocates past obstacles on DNA.

Discussion

A mutant of streptavidin, traptavidin (S52G R53D), with improved biotin binding has been developed. Mutants S52G R53S and S52G R53N were also developed with lower off rates for biotin than wildtype streptavidin (FIG. 8). Traptavidin has a slower off-rate than streptavidin. Traptavidin also showed greater stability under stress, both in AFM or from a molecular motor. The fact that traptavidin binding is superior to streptavidin for biotin-4-fluorescein (FIG. 1), biotinylated BSA (FIG. 6) and biotinylated DNA (FIG. 7) indicates that traptavidin has improved binding to biotin conjugates in general rather than a certain feature of one particular ligand.

Traptavidin was a more robust roadblock to FtsK50C than streptavidin, consistent with the results from AFM. Optical tweezers showed that FtsK has a stall force of >65 pN (Pease et al., 2005, Science, 307, 586-590), so the force generated by FtsK is in the same range as indicated by AFM (FIG. 6) for inducing dissociation from biotin, although it is hard to calculate what is the equivalent loading rate for FtsK. Streptavidin has previously been used as an obstacle to molecular motors (Morris et al., 2001, Methods, 23, 149-159; Schwartz et al., 2007, J. Biol. Chem., 282, 31469-31476; Fujita and Silver, 1993, Biotechniques, 14, 608-617; Korten and Diez, 2008, Lab Chip, 8, 1441-1447), providing a much simpler means to probe force generation than single molecule assays (Pease et al., 2005, supra). However, only wild-type streptavidin has been used as a force probe, so the stronger traptavidin shown here and the range of weaker streptavidin mutants generated by ourselves and others (Laitinen et al., 2006, supra) could act as a calibration curve for force-generating proteins (Crozat et al, 2010, EMBO J., 29, 1423-1433).

Traptavidin is a tetramer but its valency could be controlled precisely between 1 and 4, using the same strategy as for streptavidin (Howarth et al., 2006, supra). Since traptavidin is expressed in comparable yield to streptavidin and since recombinant expression of streptavidin can be as efficient as isolation from *Streptomyces avidinii* (Gallizia et al., 1998, Protein Expr. Purif., 14, 192-196; Humbert et al., 2008, Methods Mol. Biol., 418, 101-110), traptavidin has potential to replace streptavidin in many of its diverse applications. The slower on-rate of traptavidin, however, means that longer incubations will be required for binding to reach equilibrium. As well as the described limitations of streptavidin in imaging and nanotechnology, dissociation is a consideration for streptavidin's applications in ligand immobilization, such as for surface plasmon resonance, especially after drying, such as in biomolecule arrays (Xia et al., 2004, Langmuir, 20, 3710-3716) or point-of-care diagnostics (Kalogianni et al., 2007, Nucleic Acids Res., 35, e23).

| SEQUENCE LISTING FREE TEXT | |
|---|---|
| SEQ ID NO: 4 | <223> Streptavidin core subunit sequence with C-terminal His tag |
| SEQ ID NO: 5 | <223> Mutant streptavidin |
| SEQ ID NO: 6 | <223> Mutant streptavidin |
| SEQ ID NO: 7 | <223> Mutant streptavidin |
| SEQ ID NO: 8 | <223> Mutant streptavidin with C-terminal His tag |
| SEQ ID NO: 9 | <223> Peptide ligand for streptavidin |
| | <222> (2) ... (2) |

| SEQUENCE LISTING FREE TEXT | |
|---|---|
| | <223> X at position 2 is an arbitrary amino acid |
| | <222> (7) ... (8) |
| | <223> Xs at positions 7 and 8 either both denote Gly; or X8 denotes Glu and X9 denotes Arg or Lys |
| SEQ ID NO: 10 | <223> Synthetic primer |
| SEQ ID NO: 11 | <223> Synthetic primer |
| SEQ ID NO: 12 | <223> Synthetic primer |
| SEQ ID NO: 13 | <223> Synthetic primer |
| SEQ ID NO: 14 | <223> Synthetic primer |
| SEQ ID NO: 15 | <223> Acceptor peptide |
| SEQ ID NO: 16 | <223> Synthetic primer |
| SEQ ID NO: 17 | <223> Synthetic primer |

The invention claimed is:

1. A mutant streptavidin subunit which comprises one or more amino acid substitutions compared to a wildtype streptavidin subunit at any one or more of residue positions equivalent to positions 52, 53, 50, 51 and 54 of SEQ ID NO: 2 and wherein amino acid residues at positions equivalent to positions 23, 27, 43, 45, 49, 79, 88, 90, 92, 108, 110 and 128 of SEQ ID NO: 2, in said mutant streptavidin subunit, are wildtype, wherein
  (i) when said mutant streptavidin subunit is in a streptavidin tetramer, said streptavidin has a lower off rate for biotin or for a biotin conjugate than wildtype streptavidin,
  or
  (ii) when said mutant streptavidin subunit is in monomeric form, said mutant monomeric streptavidin has a lower off rate for biotin or a biotin conjugate than monomeric streptavidin, and
  wherein the amino acid residue at the position equivalent to position 52 of SEQ ID NO. 2 is substituted with glycine and the amino acid residue at the position equivalent to position 53 of SEQ ID NO. 2 is substituted with aspartic acid.

2. The mutant streptavidin subunit of claim 1 wherein said subunit is at least 70% identical to the wildtype streptavidin subunit sequence as set forth in SEQ ID NO: 1, 2 or 3.

3. The mutant streptavidin subunit of claim 1 wherein said subunit is conjugated to a molecule or is immobilised to a solid support.

4. A mutant streptavidin comprising at least one mutant streptavidin subunit of claim 1.

5. A mutant streptavidin comprising four mutant streptavidin subunits of claim 1.

6. A mutant streptavidin subunit of claim 1 wherein said subunit is in monomeric form.

7. A nucleic acid molecule comprising a nucleotide sequence which encodes the mutant streptavidin subunit of claim 1.

8. A vector comprising the nucleic acid molecule of claim 7.

9. A cell comprising the nucleic acid of claim 7.

10. A process for producing the mutant streptavidin subunit of claim 1 comprising the steps of:
  a) transforming or transfecting a host cell with a vector which comprises a nucleotide sequence encoding the mutant streptavidin subunit;
  b) culturing the host cell under conditions which allow the expression of the streptavidin mutant subunit; and
  c) isolating the mutant streptavidin subunit.

11. A kit comprising the mutant streptavidin subunit of claim 1.

12. A method of capturing a biotinylated molecule or cell comprising the step of passing said biotinylated molecule or cell over an immobilised mutant streptavidin subunit as defined in claim 1.

13. The mutant streptavidin subunit of claim 1 conjugated to a therapeutic agent for use in therapy wherein said mutant streptavidin subunit targets said therapeutic agent to a biotinylated cell.

* * * * *

SEQUENCE LISTING

```
<160> NUMBER OF SEQ ID NOS: 17

<210> SEQ ID NO 1
<211> LENGTH: 183
<212> TYPE: PRT
<213> ORGANISM: Streptomyces avidinii

<400> SEQUENCE: 1

Met Arg Lys Ile Val Val Ala Ala Ile Ala Val Ser Leu Thr Thr Val
1               5                   10                  15

Ser Ile Thr Ala Ser Ala Ser Ala Asp Pro Ser Lys Asp Ser Lys Ala
                20                  25                  30

Gln Val Ser Ala Ala Glu Ala Gly Ile Thr Gly Thr Trp Tyr Asn Gln
            35                  40                  45

Leu Gly Ser Thr Phe Ile Val Thr Ala Gly Ala Asp Gly Ala Leu Thr
        50                  55                  60

Gly Thr Tyr Glu Ser Ala Val Gly Asn Ala Glu Ser Arg Tyr Val Leu
65                  70                  75                  80

Thr Gly Arg Tyr Asp Ser Ala Pro Ala Thr Asp Gly Ser Gly Thr Ala
                85                  90                  95

Leu Gly Trp Thr Val Ala Trp Lys Asn Asn Tyr Arg Asn Ala His Ser
            100                 105                 110

Ala Thr Thr Trp Ser Gly Gln Tyr Val Gly Gly Ala Glu Ala Arg Ile
        115                 120                 125

Asn Thr Gln Trp Leu Leu Thr Ser Gly Thr Thr Glu Ala Asn Ala Trp
130                 135                 140

Lys Ser Thr Leu Val Gly His Asp Thr Phe Thr Lys Val Lys Pro Ser
145                 150                 155                 160

Ala Ala Ser Ile Asp Ala Ala Lys Lys Ala Gly Val Asn Asn Gly Asn
                165                 170                 175

Pro Leu Asp Ala Val Gln Gln
            180

<210> SEQ ID NO 2
<211> LENGTH: 159
<212> TYPE: PRT
<213> ORGANISM: Streptomyces avidinii

<400> SEQUENCE: 2

Asp Pro Ser Lys Asp Ser Lys Ala Gln Val Ser Ala Ala Glu Ala Gly
1               5                   10                  15
```

```
Ile Thr Gly Thr Trp Tyr Asn Gln Leu Gly Ser Thr Phe Ile Val Thr
             20                  25                  30

Ala Gly Ala Asp Gly Ala Leu Thr Gly Thr Tyr Glu Ser Ala Val Gly
         35                  40                  45

Asn Ala Glu Ser Arg Tyr Val Leu Thr Gly Arg Tyr Asp Ser Ala Pro
 50                  55                  60

Ala Thr Asp Gly Ser Gly Thr Ala Leu Gly Trp Thr Val Ala Trp Lys
 65                  70                  75                  80

Asn Asn Tyr Arg Asn Ala His Ser Ala Thr Thr Trp Ser Gly Gln Tyr
                 85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 3
<211> LENGTH: 127
<212> TYPE: PRT
<213> ORGANISM: Streptomyces avidinii

<400> SEQUENCE: 3

Ala Glu Ala Gly Ile Thr Gly Thr Trp Tyr Asn Gln Leu Gly Ser Thr
 1               5                  10                  15

Phe Ile Val Thr Ala Gly Ala Asp Gly Ala Leu Thr Gly Thr Tyr Glu
             20                  25                  30

Ser Ala Val Gly Asn Ala Glu Ser Arg Tyr Val Leu Thr Gly Arg Tyr
         35                  40                  45

Asp Ser Ala Pro Ala Thr Asp Gly Ser Gly Thr Ala Leu Gly Trp Thr
 50                  55                  60

Val Ala Trp Lys Asn Asn Tyr Arg Asn Ala His Ser Ala Thr Thr Trp
 65                  70                  75                  80

Ser Gly Gln Tyr Val Gly Gly Ala Glu Ala Arg Ile Asn Thr Gln Trp
                 85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 4
<211> LENGTH: 133
<212> TYPE: PRT
<213> ORGANISM: Artificial
<220> FEATURE:
<223> OTHER INFORMATION: Streptavidin core subunit sequence with C-
      terminal His tag

<400> SEQUENCE: 4

Ala Glu Ala Gly Ile Thr Gly Thr Trp Tyr Asn Gln Leu Gly Ser Thr
 1               5                  10                  15

Phe Ile Val Thr Ala Gly Ala Asp Gly Ala Leu Thr Gly Thr Tyr Glu
             20                  25                  30

Ser Ala Val Gly Asn Ala Glu Ser Arg Tyr Val Leu Thr Gly Arg Tyr
         35                  40                  45
```

```
Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser His
            115                 120                 125

His His His His His
            130

<210> SEQ ID NO 5
<211> LENGTH: 127
<212> TYPE: PRT
<213> ORGANISM: Artificial
<220> FEATURE:
<223> OTHER INFORMATION: Mutant streptavidin

<400> SEQUENCE: 5

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
                20                  25                  30

Ser Ala Val Gly Asn Ala Glu Gly Asp Tyr Val Leu Thr Gly Arg Tyr
            35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
            115                 120                 125

<210> SEQ ID NO 6
<211> LENGTH: 127
<212> TYPE: PRT
<213> ORGANISM: Artificial
<220> FEATURE:
<223> OTHER INFORMATION: Mutant streptavidin

<400> SEQUENCE: 6

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
                20                  25                  30

Ser Ala Val Gly Asn Ala Glu Gly Ser Tyr Val Leu Thr Gly Arg Tyr
            35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95
```

-continued

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
            115                 120                 125

<210> SEQ ID NO 7
<211> LENGTH: 127
<212> TYPE: PRT
<213> ORGANISM: Artificial
<220> FEATURE:
<223> OTHER INFORMATION: Mutant streptavidin

<400> SEQUENCE: 7

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Gly Asn Tyr Val Leu Thr Gly Arg Tyr
            35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
            115                 120                 125

<210> SEQ ID NO 8
<211> LENGTH: 133
<212> TYPE: PRT
<213> ORGANISM: Artificial
<220> FEATURE:
<223> OTHER INFORMATION: Mutant streptavidin with C-terminal His tag

<400> SEQUENCE: 8

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Gly Asp Tyr Val Leu Thr Gly Arg Tyr
            35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser His
            115                 120                 125

His His His His His
        130

<210> SEQ ID NO 9
<211> LENGTH: 8

```
<212> TYPE: PRT
<213> ORGANISM: Artificial
<220> FEATURE:
<223> OTHER INFORMATION: Peptide ligand for streptavidin
<220> FEATURE:
<221> NAME/KEY: VARIANT
<222> LOCATION: (2)..(2)
<223> OTHER INFORMATION: X at position 2 is an arbitrary amino acid
<220> FEATURE:
<221> NAME/KEY: VARIANT
<222> LOCATION: (7)..(8)
<223> OTHER INFORMATION: Xs at positions 7 and 8 either both denote Gly;
      or X8 denotes Glu and X9 denotes Arg or Lys

<400> SEQUENCE: 9

Trp Xaa His Pro Gln Phe Xaa Xaa
1               5

<210> SEQ ID NO 10
<211> LENGTH: 51
<212> TYPE: DNA
<213> ORGANISM: Artificial
<220> FEATURE:
<223> OTHER INFORMATION: Synthetic primer

<400> SEQUENCE: 10
gaatccgctg ttggtaacgc tgaaggcgat tacgttctga ccggtcgtta c            51

<210> SEQ ID NO 11
<211> LENGTH: 18
<212> TYPE: DNA
<213> ORGANISM: Artificial
<220> FEATURE:
<223> OTHER INFORMATION: Synthetic primer

<400> SEQUENCE: 11
gctagcgccg ccaccatg                                                 18

<210> SEQ ID NO 12
<211> LENGTH: 65
<212> TYPE: DNA
<213> ORGANISM: Artificial
<220> FEATURE:
<223> OTHER INFORMATION: Synthetic primer

<400> SEQUENCE: 12
cactcgatct tctgggcctc gaagatatcg ttcaggccgc caatctctcc actcgtcggc   60
cagag                                                               65

<210> SEQ ID NO 13
<211> LENGTH: 63
<212> TYPE: DNA
<213> ORGANISM: Artificial
<220> FEATURE:
<223> OTHER INFORMATION: Synthetic primer

<400> SEQUENCE: 13
gaggcccaga agatcgagtg gcacgagggc agtgaaggat ctggcgaaat ctgcgggcca   60
ggc                                                                 63

<210> SEQ ID NO 14
<211> LENGTH: 22
<212> TYPE: DNA
<213> ORGANISM: Artificial
<220> FEATURE:
<223> OTHER INFORMATION: Synthetic primer

<400> SEQUENCE: 14
```

```
gattgcggcc gctcagcagg tc                                             22

<210> SEQ ID NO 15
<211> LENGTH: 15
<212> TYPE: PRT
<213> ORGANISM: Artificial
<220> FEATURE:
<223> OTHER INFORMATION: Acceptor peptide

<400> SEQUENCE: 15

Gly Leu Asn Asp Ile Phe Glu Ala Gln Lys Ile Glu Trp His Glu
1               5                   10                  15

<210> SEQ ID NO 16
<211> LENGTH: 19
<212> TYPE: DNA
<213> ORGANISM: Artificial
<220> FEATURE:
<223> OTHER INFORMATION: Synthetic primer

<400> SEQUENCE: 16
cggagacggt cacagcttg                                                 19

<210> SEQ ID NO 17
<211> LENGTH: 19
<212> TYPE: DNA
<213> ORGANISM: Artificial
<220> FEATURE:
<223> OTHER INFORMATION: Synthetic primer

<400> SEQUENCE: 17
cggctcgtat gttgtgtgg                                                 19
```